US006175059B1

(12) United States Patent
Rush

(10) Patent No.: US 6,175,059 B1
(45) Date of Patent: Jan. 16, 2001

(54) DEVELOPMENT OF A NOVEL GENE DELIVERY SYSTEM THROUGH SEED COATING

(75) Inventor: Charles M. Rush, Amarillo, TX (US)

(73) Assignee: Texas A & M University, College Station, TX (US)

(*) Notice: Under 35 U.S.C. 154(b), the term of this patent shall be extended for 0 days.

(21) Appl. No.: 08/822,124

(22) Filed: Mar. 21, 1997

(51) Int. Cl.[7] .......................... A01N 63/00; A01N 63/04; A01H 5/10; A01H 1/00

(52) U.S. Cl. .......................... 800/279; 800/278; 435/468; 435/254.11; 427/4; 424/93; 424/93.2; 424/93.21; 424/93.5

(58) Field of Search ............................. 47/57.6; 800/250, 800/DIG. 52, 278, 279; 427/4; 435/254.11, 468; 424/93.2, 93.21, 93.5

(56) References Cited

FOREIGN PATENT DOCUMENTS 3-277273 9/1991 (JP) .

OTHER PUBLICATIONS

Plant Pathology. 1978. Agrios G. Chapter 14: Plant diseases caused by viruses.*
Dessens and Meyer. Virus Gene. 1996. vol. 121: 95–99.*
Nejidat et al. Physiologia Plantarum. 1990. vol. 80: 662–668.*
The Plant Virus. Editted by: Van Regenmortel and Fraenkel–Conrat. vol. 2. 1986. Chapter: 16, pp. 305–335.*
Ahlquist, P., R. French, M. Janda, L.S. Loesch–Fries. 1984. Multicomponent RNA plant virus infection derived from cloned viral cDNA, P.N.A.S. USA 81:7066–7070.
Barr, D.J.S. 1979. Morphology and host range of *Polymyxa graminis, Polymyxa betae,* and *Ligniera pilorum* from Ontario and some other areas. Can.J. Plant Pathol. 1:85–94.
Barr, D.J.S. 1988. Zoosporic plant parasites as fungal vectors of viruses: Taxonomy and life cycles of species involved. pp. 123–137 In: Development in Applied Biology 2, Viruses and Fungal Vectors, J.I. Cooper and M.J.C. Asher, eds. Univ. of St. Andrews, UK.
Barr, K.J. and M.J.C. Asher. 1992. The host range of *Polymyxa betae* in Britain. Plant Pathol. 41:64–68.

Beachy, R.N., S. Loesch–Fries, and N.E. Tumer. 1990. Coat protein–mediated resistance against virus infection. Annu. Rev. Phytopathol. 28:451–474.

Bouzoubaa, S., H. Guilley, G. Jonard, I. Jupin, L. Quillet, K. Richards, D. Scheidecker, and V. Ziegler–Graff. 1988. Genome organization and function of beet necrotic yellow vein virus. Develop. Appl. Biol. 2:99–110.
Bouzoubaa, S., L. Quillet, H. Guilley, G. Jonard, and K. Richards. 1987. Nucleotide sequence of beet necrotic yellow vein virus RNA–1. J. Gen. Virol. 68:615–626.
Bouzoubaa, S., V. Ziegler, D. Beck, H. Guilley, K. Richards, and G. Jonard. 1986. Nucleotide sequence of beet necrotic yellow vein virus RNA–2. J. Gen. Virol. 67:1689–1700.
Bouzoubaa, S., H. Guilley, G. Jonard, K. Richards, and C. Putz. 1985. Nucleotide sequence analysis of RNA–3 and RNA–4 of beet necrotic yellow vein virus, isolates F2 and G1. J. Gen. Virol. 66:1553–1564.
Boyer, J.C. and A.L. Haenni. 1994. Infectious transcripts and cDNA clones of RNA viruses. Virology 198:415–426.
Brisson N., J. Paszkowski, J.R. Penswick, B. Gronenborn I. Potrykus and T. Hohn. 1984. Expression of a bacterial gene in plants by using a viral vector. Nature 310;511–514.
Brunt, A.A., and K.E. Richards. 1989. Biology and molecular biology of furoviruses. Adv. Virus Res. 36:1–32.
Brunt, A.A., E. Shikata. Fungus–transmitted and similar labile rod–shaped viruses. In: The Plant Viruses: vol. 2, The Rod–Shaped Plant Viruses. M.H.V. Van Regenmortel and Heinz Fraenkel–Conrat, eds. Plenum Press, NY. pp. 305–335.
Chapman, S., T. Kavanagh and D. Baulcombe. 1992. Potato virus X as a vector for gene expression in plants. Plant J. 2:549–557.
Christensen A.H. and P.H. Quail. 1996. Ubiquitin promoter–based vectors for high–level expression of selectable and/or screenable marker genes in monocotyledonous plants. Transg. Res. 5:213–218.
Christou, P., D.G. McCabe, and W.F. Swain. 1988. Stable transformation of soybean callus by DNA–coated gold particles. Plant Physiol. 87:671–674.

D'Halliun, K., E. Bonne, M. Bossut, and M. DeBeuckeleer and H. Leemans. 1992. Transgenic maize plants by tissue electroporation. Plant Cell 4:1495–1505.

Datta, S.K., A. Peterhans, K. Datta and C. Potrykus. 1990. Genetically engineered fertile Indica rice recovered from protoplasts. Bio/Technol. 8:736–740.
Dawson, W.O., P.Bubrick and G.L. Grantham. 1988. Modifications of the tobacco mosaic virus coat protein gene affecting replication, movement, and symptomatology. Phytopathol. 78:783–789.
De Block, M., J. Botterman, M. Vandiwiele, J. Dockx, C. Thoen, V. Gosselle, N. Rao Movva, C. Thompson, M. Van Montagu, and J. Leemans. 1987. Engineering herbicide resistance in plants by expression of a detoxifying enzyme. EMBO J. 6:2513–2518.

(List continued on next page.)

*Primary Examiner*—Paula K. Hutzell
*Assistant Examiner*—Ousama M-Faiz Zaghmout
(74) *Attorney, Agent, or Firm*—Fulbright & Jaworski, L.L.P.

(57) ABSTRACT

This invention describes a novel means of introducing foreign genes and/or viruses, wildtype or recombinant, into plant cells via a seed treatment method using recombinant or wildtype furoviruses and their natural fungal vectors. Because of its ease of application, longevity of the seed treatment product, minimal risk of transmission to subsequent seed generations, specificity, and universality within a species, it offers a significant improvement over prior art techniques for viral mediated gene delivery techniques. The unique and critical aspect of the invention is the use of seed treatment technology for delivering foreign genes or viruses into plants for, for example, the enhancement of agronomic traits and production of desirable products such as pharmaceuticals.

11 Claims, No Drawings

OTHER PUBLICATIONS

De la Pena, A., H. Lorz, and J. Schell. 1987. Transgenic rye plants obtained by injecting DNA into young floral tillers. Nature 325:274–276.

Dellacioppa G. 1996. Production of biopharmaceuticals in higher plants by transfection with RNA viral vectors. In Vitro 32:22A.

Deom, C.M., M.J. Oliver, and R.N. Beachy. 1987. The 30–kilodalton gene product of tobacco mosaic virus potentiates virus movement. Science 237:389–394.

Dinant, S., F. Blaise, C. Kusiak, S. Astier–Manifacier, and J. Albouy. 1993. Heterologous resistance to potato virus Y in transgenic tobacco plants expressing the coat protein gene of lettuce mosaic potyvirus. Phytopathol. 83:818–824.

Dolja, V.V., H.J. McBride, J.C. Carrington. 1992. Tagging of plant and potyvirus replication and movement by insertion of β–glucuronidase into the viral polyprotein. P.N.A.S. USA 89:10208–10212.

Donson, J., C.M. Kearney, M.E. Hilf, and W.O. Dawson. 1991. Systemic expression of a bacterial gene by a tobacco mosaic virus–based vectors. P.N.A.S. USA 88:7204–7208.

Duffus, J.E., and H.Y. Liu. 1987. First report of rhizomania of sugar beet from Texas. Plant Dis. 71:557.

Dunwell, J.M. 1985. Anther and ovary culture In. Cereal Tissue and Cell Culture, S W. J. Bright and M. G. K. Jones, eds., Martinus Nijhoff/W. Junk, Dorbrecht. pp. 1–44.

Fauquet, C., D. Desbois, D. Fargette, and G. Vidal. 1988. Classification of furoviruses based upon the amino acid composition of their coat proteins. In.: Development in Applied Biology 2, Viruses with Fungal Vectors, J.I. Cooper and M.J.C. Asher, eds., Univ. of St. Andrews, UK., pp. 19–36.

Fraley, R.T., S.G. Rogers, R.B. Horsch, P.R. Sanders, J.S. Flick, S.P. Adams, M.L. Bittner, L.A. Brand, C.L. Fink, J.S. Fry, G.R. Galluppi, S.B. Goldberg, N.L. Hoffmann, and S.C. Wood. 1983. Expression of bacterial genes in plant cells. P.N.A.S. USA 80:4803–4807.

Fry, J.E., A.R. Barnason, and M. Hinchee. 1991. Genotype–independent transformation of sugar beet using *Agrobacterium tumefaciens*. In. Molecular biology and plant development, Proc. Third International Congress of the ISPMB, Tuscon, USA. Abstract No. 384.

Fulton, R.W. 1986. Practices and precautions in the use of cross protection for plant virus disease control. Ann. Rve. Phytopathol. 24:67–81.

Gera, A., C.M. Deom, J. Donson, J.J. Shaw, D.J. Lewandowski, and W.O. Dawson. 1995. Tobacco mosaic tobamovirus does not require concomitant synthesis of movement protein during vascular transport. Mol. Plant–Microbe Interact. 8:784–787.

Gerik, J.S. 1992. Zoosporic obligate parasites of roots. In: Methods for Research on Soilborne Phytopathogenic Fungi. L.L. Singleton, J.D. Milhail, and C.M. Rush (eds.). APS Press, St. Paul, MN. pp. 18–24.

Gerik, J.S., and J.E. Duffus. 1988. Differences in vectoring ability and aggressiveness of isolates of *Polymyxa betae*. Phytopathol. 78:1340–1343.

Gerik, J.S., and J.E. Duffus. 1987. Host range of California isolates of *Polymyxa betae*. Phytopathol. 77:1759.

Gruber, M. Y. and W. L. Crosby. 1993. Vectors for plant transformation. In. Methods in Plant Molecular Biology and Biotechnology, B. R. Glick, and J.E. Thompson, eds. CRC Press, Boca Raton, pp. 89–119.

Hall, R.D., T. Riksen–Bruinsma, G. J. Weyeus, I. J. Rosquin, P. N. Denys, I. J. Evans, J. E. Lathonwers, M. P. Lefebure, J. M. Dunwell, A. V. Tunen, and F. A. Krens. 1996. A high efficiency technique for the generation of transgenic sugar beets from stomatal guard cells. Nature Biotechnol. 14:1133–1138.

Harveson, R. M., and C. M. Rush. 1993. A simple method for field and greenhouse inoculation of *Polymyxa betae* and beet necrotic yellow vein virus. Phytopathol. 83:1216–1219.

Harveson, R.M., and C.M. Rush. 1993. Movement of viruliferous *Polymyxa betae* from a point source inoculation. J. Sugar Beet Res. 30:97.

Harveson, R. M., C.M. Rush, and T. A. Wheeler. 1996. The spread of beet necrotic yellow vein virus from point source inoculations as influenced by irrigation and tillage. Phytopathol. 86:1242–1247.

Hayes, R.J., R.H.A. Coutts, and K.W. Buck. 1989. Stability and expression of bacterial genes in replicating geminivirus vectors in plants. Nucleic Acids Res. 17:2391–2403.

Heidel, G. B., and C. M. Rush. 1994. Distribution of beet necrotic yellow vein virus beet distortion mosaic virus and an unnamed soilborne sugar beet virus in Texas and New Mexico. Plant Dis. 78:603–606.

Heidel, G.B. and C.M. Rush. 1995. Effects on growth of two sugar beet cultivars infected by BNYVV,BSBMV, orBNYVY + BSBMV, American Society of Sugar Beet Technologists Proc., New Orleans, LA.

Heidel, G.B., C.M. Rush, T.L. Kendall, and S.A. Lommel. 1993. Partial characterization of a soilborne sugar beet virus in Texas. J. Sugar Beet Res. 30:98.

Heidel G.B., C.M. Rush, T.L. Kendall, S.A.Lommel, and R.C. French.1996. Characteristics of beet soilborne mosaic virus, a furo–like virus infecting sugar beet. Phytopathol. (submitted).

Hiei, Y., S. Ohta, T. Komari and T. Kumasho. 1994. Efficient transformation of rice (*Oryza sativa*L.) mediated by Agrobacterium and sequence analysis of the boundaries of the T–DNA. Plant J. 6:271–282.

Horsch, R.B., J. Fry, N. L. Hoffmann, M. Wallroth, D. Eichholtz, S. G. Rogers, and R. T. Fraley, 1985. A simple and general method for transferring genes into plants. Science 227:1229–1231.

Horsch, R.B., R. T. Fraley, S.G. Rogers, H.J. Klee, J. Fry, and M. Hinchee. 1987. Agrobacterium–mediated gene transfer to plants: Problems and Prospects. In. Plant Bio/technology—Research Bottlenecks for Commercialization and Beyond, T. J. Mabry, ed., $IC^2$ Institute, Austin, TX, pp. 9–26.

Ishida Y., H. Saito, S. Ohta, Y. Hiei, T. Komari, and T. Kumashiro. 1996. High efficiency transformation of maize (*Zea mays* L.) mediated by *Agrobacterium tumefaciens*. Nature Biotechnol. 14:745–750.

Jefferson, R. A. 1987. Assaying chimeric genes in plants the gene fusion system. Plant Mol. Biol. Rep. 5:387–405.

Jupin, I., H. Guilley, K.E. Richards, and G. Jonard. 1992. Two proteins encoded by beet necrotic yellow vein virus RNA 3 influence symptom phenotype on leaves. EMBO J. 11:479–488.

Jupin, I., K. Richards, G. Jonard, H. Guilley, and C.W.A. Pleu. 1990. Mapping sequences required for productive replication of beet necrotic yellow vein virus RNA3. Virology 178:273–280.

Jupin, I., T. Tamada, and K. Richards. 1991. Pathogenesis of beet necrotic yellow vein virus. Virology 2:121–129.

Kaeppler, H.F., D.A. Somers, H.W. Rines, and A.F. Cockburn. 1992. Silicon carbide fiber–mediated stable transformation of plant cells. Theor. Appl. Genet. 84:560–566.

Kaufmann, A. et al. 1992. Single– and Double–Stranded RNAs Associated with an Isolate of Beet Soil–Borne Virus. Intervirology 33:97–102.

Kendall, T. L., et al 1988. Molecular Characterization of Sorghum Chlorotic Spot Virus, a Proposed Furovirus. J. Gen. Virol. 69:2335–2345.

Klee, H., R. Horsch, and S. Rogers. 1987. Agrobacterium-–mediated plant transformation and its further applications to plant biology. Annu. Rev. Plant Physiol. 38:467–486.

Klein, T.M., E.D.Wolf, R. Wu, and J.C. Sanford. 1987. High–velocity microprojectiles for delivering nucleic acid into living cells. Nature 327:70–73.

Koenig, R., and W. Burgermeister. 1989. Mechanical inoculation of sugarbeet roots with isolates of beet necrotic yellow vein virus having different RNA compositions. J. Phytopathol. 124:249–255.

Koenig, R., W. Burgermeister, H. Weich, W. Sebald, and C. Kothe. 1986. Uniform RNA patterns of beet necrotic yellow vein virus in sugarbeet roots, but not in leaves from several plant species. J. Gen. Virol. 67:2043–2046.

Krens, F.A., C. Zijistra, Van der Molen, W., D. Jamar, and H.J. Huizing. 1988. Transformation and regeneration in sugar beet induced by "shooter" mutants of *Agrobacterium tumefaciens*. Euphytica 185–194.

Kumagai, M.H., J. Donson, G. Delta–Cioppa, D. Harvey, K. Hanley, and L.K. Grill. 1995. Cytoplasmic inhibition of carotenoid biosynthesis with virus–derived RNA. P.N.A.S. USA 92:1679–1683.

Kuszala, M., V. Ziegler, S. Bouzoubaa, K. Richards, C. Putz, H. Guilley, and G. Jonard. 1986. Beet necrotic yellow vein virus: Different isolates are serollogically similar but differ in RNA composition. Ann. Appl. Biol. 109:155–162.

Lazzeri, P.A. and P.R. Shewry. 1993. Biotechnology of cereals. In. Biotechnology and Genetic Engineering Review. 11:79–146.

Lemaire, O., D. Merdinoglu, P. Valentin, C. Putz, V. Ziegler–Graff, H. Guilley, G. Jonard, and K. Richards. 1988. Effect of beet necrotic yellow vein virus RNA composition on transmission by *Polymyxa betae*. Virology 162:232–235.

Liu, H.–Y., and J.E. Duffus. 1988. The occurrence of a complex of viruses associated with rhizomania of sugarbeet. Phytopathol. 78:1583 (Abst).

Lovic, B. R. and C.M. Rush. 1995. BNYVV–related indigenous mild viral strains for biocontrol of rhizomania: Characterization of candidate isolates and production of inoculum for field testing. Phytopathol. 85:1136.

Luo, Z. and R. Wu. 1988. A simple method for the transformation of rice via the pollen–tube pathway. Plant Mol. Biol. Rep. 6:165–174.

Maas, C. and W. Werr. 1989. Mechanism and optimized conditions for PEG mediated DNA transfection into plant pitoplasts. Plant Cell Rep. 8:148–151.

Matthews, R.E.F. 1991. In Plant Virology Third Edition, Academic Press, Inc. Harcourt Brace Jovanovich Publishers, pp. 346–348.

McCormick, S., J. Niedermeyer, J. Fry, A. Barnason, R. Horsch, and R. Fraley. 1986. Leaf disc transformation of cultivated tomato (*L. esculentum*) using *Agrobacterium tumefaciens*. Plant Cell Rep. 51:81–84.

Ooms, G. 1992. Genetic engineering of plants and cultures. In. Plant Biotechnology, M. W. Fowler and G. S. Warren, eds. Pergamon Press, Oxford, pp. 223–257.

Peters, D., and A. Godfrey–Veltman. 1989. *Polymyxa betae* zoospores as vectors of beet necrotic yellow vein furovirus. Bull. OEPP/EPPO 19:509–515.

Prillwitz, H., and E. Schlosser. 1993. In: Proc. Second Symposium International Working Group on Plant Viruses with Fungal Vectors, Montreal, Canada, pp. 71–74.

Prillwitz, H., and E. Schlosser. 1993. Virus–vector interactions in the Rhizomania syndrome. In: Proc. Second Symposium International Working Group on Plant Viruses with Fungal Vectors, Montreal, Canada, pp. 107–110.

Putz, C. 1977. Composition and Structure of Beet Necrotic Yellow Vein Virus. J. General Virology 35:397–401.

Quillet, L., H. Guilley, G. Jonard, and K. Richards. 1989. In vitro synthesis of biologically active beet necrotic yellow vein virus RNA. Virology 172:293–301.

Raineri, D.M., P. Bottino, M.P. Gordon, and N.W. Nester. 1990. Agrobacterium–mediated transformation of rice (*Oryza sativa* L.) Bio/Technol. 8:33–38.

Richards, K., G. Jonard, H. Guilley, V. Ziegler, and C. Putz. 1985. In vitro translation of beet necrotic yellow vein virus RNA and studies of sequence homology among the RNA species using cloned cDNA probes. J. Gen. Virol. 66:345–350.

Richards, K. E., and T. Tamada. 1992. Mapping functions on the multipartite genome of beet necrotic yellow vein virus. Annu. Rev. Phytopathol. 30:291–313.

Rush, C. M., G.B. Heidel, R. C. French, and M.D. Lazar. 1993. Relationship between BNYVV and an unnamed soil-borne sugar beet virus from Texas. J. Sugar Beet Res. 30:114.

Rush, C.M., R.C. French, and G.B. Heidel. 1993. Texas 7 a possible strain of beet necrotic yellow vein virus. In Proceedings Second Symposium International Working Group on Plant Viruses with Fungal Vectors, Montreal, Canada, pp. 59–62.

Rush, C.M., R.C. French, and G.B. Heidel. 1994. Differentiation of two closely related furoviruses using the polymerase chain reaction. Phytopathol. 84:1366–1369.

Rush, C.M. and G.B. Heidel. 1995. Furovirus diseases of sugar beets in the United States. Plan Dis. 79:868–875.

Rush, C.M., G. B. Heidel, and M.D. Laar. 1993. Relationship between BNYVV and an unnamed soilborne sugar beet virus from Texas. American Society of Sugar Beet Technologists Proc., Anaheim, CA, 30:114.

Rush, C.M., K.–B.G. Scholthof, S.K. Manohar, and G.B. Heidel. 1996. Similarities between beet soilborne mosaic virus and beet necrotic yellow vein virus RNA2 nucleotide sequence and genomic organization. In: Proceedings Third Symposium international Working Group on Plant Viruses with Fungal Vectors, J. Sherwood and C. Rush, eds., C&M Press, Denver, CO. (in press).

Rush, C.M. and J.L. Sherwood. 1996. Viral control agents. In: Environmentally Safe Approaches to Crop Disease Control, Chapter 6, J. Rechcigl, ed., CRC Press, Boca Raton, FL (in press).

Ryals, J. 1996. Agricultural biotechnology '96. Mol. Breed. 2:91–93.

Sambrook, J., E. F. Fritsch, and T. Maniatis. 1989. Molecular Cloning: A Laboratory Manual, 2nd ed., Cold Spring Harbor Laboratory Press, Plainview, NY.

Sanford, J.C. 1988. The biolistic process. Trends in Bio Tech. 6:299–302.

Schmitt, C., E. Balmori, G. Jonard, K.E. Richrads, and H. Guilley. 1992. In vitro mutagenesis of biologically active transcripts of beet necrotic yellow vein virus RNA 2: Evidence that a domain of the 75–kDa readthrough protein is important for efficient virus assembly. P.N.A.S. USA. 89:5715–5719.

Scholthof, H.B., K.–B.G. Scholthof and A.O. Jackson. 1996. Plant virus gene vectors for transient expression of foreign proteins in plants. Ann. Rev. Phytopathol. 34:299–323.

Senaratra, T., B.D. McKersie, K.J. Kasha, and J.D. Procunier. 1991. Direct DNA uptake during the imbibition of dry cells. Plan Sci. 79:223–228.

Shen, W.H., and B. Hohn. 1995. Vectors based on maize streak virus can replicate to high copy numbers in maize plants. J. Gen. Virol. 76:965–969.

Shepherd, R.J. 1989. Biochemistry of DNA plant viruses. In.Biochemistry of Plants. A. Marcus, ed., New York Academic Press, 15:563–616.

Shepherd, R.J., R.J. Wakeman, R. R. Romanko, 1968, DNA in cauliflower mosaic virus. Virology 36:150–152.

Sherwood, J.L. 1987. Mechanisms of cross–protection between plant virus strains. In: Plant Resistance to Viruses. D. Evered and S. Harnett, eds., Wiley. Chichester, pp. 136–150.

Shirako, Y., and M.K. Brakke. 1984. Two purified RNAs of soil–borne wheat mosaic virus are needed for infection. J. Gen. Virol. 65:119–127.

Simon, A.E. and J.J. Bujarski. 1994. RNA–RNA recombination and evolution in virus–infected plants. Ann. Rev. Phytopathol. 32:337–362.

Somers, D.A., H.W. Rines, W. Gu, H.F. Kaeppler, and W.R. Bushnell. 1992. Fertile transgenic oat plants. Bio/Technol. 10:1589–1594.

Stanley, J. 1993. Gemini viruses: plant viral vectors. Curr. Opin. Genet. Dev. 3:91–96.

Tamada, T., M. Saito, T. Kiguchi, T. Kusume. 1990. Effect of isolates of beet necrotic yellow vein virus with different RNA components on the development of rhizomania symptoms. In: Proc. First Symposium international Working Group on Plant Viruses with Fungal Vectors, Braunschweig, Germany, pp. 41–44.

Tamada, T., Y. Shirako, H., Abe, M. Saito, T. Kiguchi, and T. Harada. 1989. Production and pathogenicity of isolates of beet necrotic yellow vein virus with different numbers of RNA components. J. Gen. Virol. 70:3399–3409.

Tamada, T. 1975. Beet necrotic yellow vein virus. Commonwealth Mycol. Inst. Assoc. Appl. Biol. 144, Wm Culross and Son Ltd., Scotland.

Topfer, R., B. Gronenborn, J. Shell, and H.H. Steinbiss. 1989. Uptake and transient expression of chimeric genes in seed–derived embryos. Plant Cell. 2:133–139.

Tuitert, G. 1993. Horizontal spread of beet necrotic yellow vein virus in soil. Neth. J. Plant Pathol. 99:85–96.

Van der Kuyl, A.C., L. Neelman, and J.F. Bol. 1991. Complementation and recombination between alfalfa mosaic virus RNA3 mutants in tobacco plants. Virology 183:731–738.

Vasil, V., A. Castillo, M. Fromm, and I. Vasil. 1992. Herbicide resistant fertile transgenic wheat plants obtained by microprojectile bombardment of regenerable embryogenic callus. Bio/Technology 10:667–674.

Weeks, J. T., O.D. Anderson, and A.E. Blechl. 1993. Rapid production of multiple independent lines of fertile transgenic wheat (*Triticum aestivum*). Plant Physiol. 102:1077–1084.

Wilson, S.M., T.A. Thorpe, and M.M. Moloney. 1989. PEG–mediated expression of GUS and CAT genes in protoplasts from embryogenic suspension cultures of *Picea glanca*. Plant Cell Rep. 7:704–707.

Wisler, G.C., J.E. Duffus, and H.–Y. Liu. 1993. Variations among furoviruses associated with sugarbeet. In: Proc. Second Symposium of the International Working Group on Plant Viruses with Fungal Vectors, Montreal, Canada, pp. 63–66.

Wright, M.S., K. Launis, C. Bouman, M. Hill, J. Dimatio, C. Kramer, and R.D. Shillito. 1996. A rapid visual method to identify transformed plants. In Vitro Cell and Devel. Biol. 32:11–13.

Wu, G., Shortt, B. J., Lawrence, E. B., Levin, E. B., Fitzsimmons, K. C., and Shah, D. M. 1995. Disease resistance conferred by expression of a gene encoding $H2O2$–generating glucose oxidase in transgenic potato plants.

Yang, N.S. 1995. Particle bombardment technology for gene transfer into plant and mammalian systems. In Vitro Cell. and Devel. Biol. 31, 3. A:JS–6.

Zhang, L., A. Mitra, R.C. French, and W.G. Langenberg. 1994. Fungal zoospore–mediated delivery of a foreign gene to wheat roots. Phytopathol. 84:684–687.

Ziegler–Graff, V., S., Bouzoubaa, I. Jupin, H. Guilley, G. Jonard, and K. Richards. 1988. Biologically active transcripts of beet necrotic yellow vein virus RNA–3 and RNA–4. J. Gen Virol. 69:2347–2357.

H. Barker et al., Transgenic Resistance to Potato MOP–TOP Furovirus, Proceedings of the 3d Symposium of the Inter. Working Group on Plant Viruses with Fungal Vectors 133–6 (1996).

M. Arli, et al., Studies on Potato MOP–TOP Virus Replication, Proceedings of the 3d Symposium of the Inter. Working Group on Plant Viruses with Fungal Vectors 57–60 (1996).

E. Makarainen et al., Incidence of Infection with *Spongospora Subterranea*, the Vector of Potato MOPTOP Virus, in Four Wild Potato Species, Proceedings of the 2d Symposium of the Inter. Working Group on Plant Viruses with Fungal Vectors 111–4 (1993).

B. Reavy et al., Potato MOP–TOP Virus: A Third Type of Furovirus Genome Organisation, Proceedings of the 2d Symposium of the Inter. Working Group on Plant Viruses with Fungal Vectors 23–6 (1993).

I. Ahmad et al., The Presence of *Spongospora Subterranea* F.SP. Subterranea in the Northern Areas of Pakistan Confirmed by Microrscopy, Serology and Bioassay, Proceedings of the 3d Symposium of the Inter. Working Group on Plant Viruses with Fungal Vectors 117–20 (1996).

U. Merz et al., Serological Detection of *Spongospora Subterranea* F.SP. Subterranea, Proceedings of the 3d Symposium of the Inter. Working Group on Plant Viruses with Fungal Vectors 169–72 (1996).

Eugene I. Savenkov et al., Analysis of the Genomic Structure and Phylogeny of Potato MOP–TOP Virus (PMTV), Proceedings of the $4^{th}$ Symposium of the Inter. Working Group on Plant Viruses with Fungal Vectors 65–8 (1999).

Maria Sandgren, Nordic Isolates of Potato MOP–TOP Virus, Comparison of Reactions with Monoclonal Antibodies and Observations on Spraing Systoms in Potato Cultivars, Proceedings of the 2d Symposium of the Inter. Working Group on Plant Viruses with Fungal Vectors 75–8 (1993).

U. Merz, Epidemiological Aspects of Powdery Scab of Potatoes Caused by *Spongospora Subterranea,* Proceedings of the 2d Symposium of the Inter. Working Group on Plant Viruses with Fungal Vectors 103–5 (1993).

J.A. Walsh et al., A Summary of Research on Watercress Yellow Spot Virus and its Fungal Vector *Spongospora Subterranea* F. Sp. Nasturtii, Proceedings of the 2d Symposium of the Inter. Working Group on Plant Viruses with Fungal Vectors 111–4 (1993).

Maria Sandgren et al., Variability Within Read–Through Region in Potato MOP–TOP Virus (PMTV) RNA 3 Among Scandinavian Isolates and Deletion Variants Detected in Test Plants and Potato Tubers, Proceedings of the $4^{th}$ Symposium of the Inter. Working Group on Plant Viruses with Fungal Vectors 61–4 (1999).

Herman B. Jackson, Plant Virus Gene Vectors for Transient Expression of Foreign Proteins in Plants, Annu. Rev. of Phytopathol, 34:299–323 (1996).

G.H. Cowan et al., Evidence that Readthrough of the Potato MOP–TOP Virus Coat Protein Gene Occurs in Plants and that the Readthrough Domain is Present at one Extremity of Some Particles, Proceedings of the 3d Symposium of the Inter. Working Group on Plant Viruses with Fungal Vectors 61–4 (1996).

N. Fornier et al., Factors Affecting the Release of Primary Zoospores from Cystosori of *Spongospora Subterranea* Assessed Using Monoclonal Antibody Elisa Test, Proceedings of the 3d Symposium of the Inter. Working Group on Plant Viruses with Fungal Vectors 89–92 (1996).

U. Merz, Microscopical Observations on Release and Morphology of and Host Infection by Primary Zoopores of *Spongospora Subterranea* F.SP. Subterranea, J. of Plant Pathology 46:670–4 (1997).

Bruce Alberts et al., *Molecular Biology of the Cell: Third Edition,* Chapter 6: Basic Genetic Mechanisms, pp 274–78 (1994).

Thomas D. Brock et al.; *Biology of Microorganisms; Sixth Edition,* Chapter 6:Viruses, pp 182–200 (1991).

\* cited by examiner

DEVELOPMENT OF A NOVEL GENE DELIVERY SYSTEM THROUGH SEED COATING

STATEMENT REGARDING FEDERALLY SPONSORED RESEARCH

Support for this research has been provided to Charles M. Rush from the USDA-NRI competitive grants program (1994–1998) and from the Texas Higher Education Development Board (1996–1997).

BACKGROUND OF THE INVENTION

1. Field of the Invention

This application incorporates by reference in its entirety U.S. patent application Ser. No. 08/299,608 now U.S. Pat. No. 5,614,186, inventor Charles M. Rush.

This invention relates to the treatment of plants to reduce the plant's susceptibility to severe disease caused by virulent viral pathogens. Plants inoculated with a non-virulent or mildly virulent virus do not express severe disease symptoms caused by the virulent virus even when co-inoculated with the virulent virus. The novel inoculation method includes application of viruliferous fungus to seeds by coating seeds with survival structures of the viruliferous fungus, such as cystosori of Polymyxa species.

In addition, the present invention relates to a method for delivering viruses, both wildtype and recombinant, to plants. Soilborne fungi containing recombinant, and/or wildtype, viruses are used to infect plants and thereby deliver recombinant and/or wildtype viruses to plants. In an embodiment of the present invention survival structures, such as cystosori, of soilborne fungi containing recombinant or wildtype viruses are used to coat seeds of plants susceptible to soilborne fungi such that plants growing from these seeds become infected with the recombinant or wildtype virus containing fungi thereby delivering the virus to the plant.

In addition, the present invention relates to a method for delivering foreign genes or viruses to plant cells. Specifically, the present invention relates to a method of introducing foreign genes or viruses into plant cells in planta, via a seed treatment method utilizing recombinant furoviruses and their natural fungal vectors in order to introduce specific agronomic traits, and production of desirable products such as pharmaceuticals.

2. General Background

Applied biotechnology in agriculture has been moving at an astonishing pace since the successful transformation of tobacco via Agrobacterium (Ti plasmid) was reported in 1983 (32). Over the last ten years, transformation of major crop species with foreign genes in order to introduce desirable agronomic traits has been a primary research focus in the scientific community. Today, new varieties have been developed from all the major crop species in which transgenic plants have been produced (65) and many of them are now available to farmers and consumers (87). The traits that have been or soon will be incorporated into crops include herbicide tolerance (Roundup, Basta, Buctril, Atrazine) insect (*Bacillus thuringiensis* endotoxin) and disease (chitinase, virus coat protein) resistance, quality improvement (high-stearic-acid oilseed rape, pre-colored cotton, and high methionine maize seed), and high-value biopharmaceutical products (alkaloids and vaccines) (24,87).

The methods for delivery of a single gene or set of genes to plant cells are known as transformation and transfection. These methods have the goal of incorporation of the alien gene(s) into plant cells or integration into the plant genome. This permits the expression of the foreign genes transiently or permanently. Transient expression describes a result of attempted transformation in which expression of the gene (production of mRNA) is time-limited, usually to a period of a few days or weeks. Reduction of expression may or may not be accompanied by loss of the gene itself. In contrast, permanent expression is accompanied by the transmission of the expressing foreign gene to subsequent generations.

Transfection is a process in which viral genes are transferred into plant cells through normal or modified virus activity. The viral genome may be modified to allow transfer of non-viral genes that replicate episomally in the cytoplasm or integrate into the plant genome (91). Transformation describes any of several other methods, both biological and physical, for the transfer of genes which are stably integrated into the genome. Such experiments sometimes result in transient expression of the gene. These methods include, but are not limited to, tissue-culture-dependent DNA delivery systems, such as Ti-plasmid (72, 76), PEG (97), $Ca^{2+}$-mediated DNA uptake through protoplasts (70), liposome encapsidation, electroporation (65), microinjection (30), silicon carbide fibers (57), particle bombardment (59), as well as other plasmid-mediated gene transfers, and tissue-culture-independent systems, such as DNA injection into ovaries (23), DNA delivery along the pollen tube (69), and DNA uptake through seed imbibition (92, 105). A necessary feature of gene delivery systems is the establishment of marker genes (NPT II, CAT, BAR, HYG, GUS and LUC) (65), promoters (NOS, CaMV 35S, Ubi 1, Adh 1, Act 1 and pEMU) and introns which, in combination with the promoter regions, facilitate the selection of transgenic plants and the expression of the foreign genes (17). In general, for all the reproducible gene transfer procedures, there are biological limitations associated with their applications, such as host specificity, genotype specificity for tissue-culture-regeneration capacity, somaclonal variation, fertility loss, insufficient level of gene expression, instability of transgenes, and potential for transfer of foreign genes into weed species (65). Most processes are highly technical, expensive, lengthy and difficult to control. At present, for dicot crops, the most efficient and widely-applicable transformation method is the Agrobacterium vector system. For monocot crops, particle bombardment of shoot tips or immature embryos is the current method of choice, even though successful Agrobacterium-mediated transformation of maize and rice have been reported (49, 52). Both procedures limit the number of genotypes that can be manipulated, dependent on their tissue-culture-regeneration capacity. Below is a more detailed description of these currently available gene transfer methods along with their limitations.

Agrobacterium-Mediated Transformation

Agrobacterium gene delivery has become almost routine in many laboratories but transformation of some species using this technology has been unsuccessful. Agrobacterium causes crown gall disease in many dicot plants in nature by transferring a defined segment of DNA from its tumor-inducing (Ti) plasmid into the nuclear genome of cells through a wound area of the plants (58). This unique plant-microbial interaction has been combined with the high totipotency of many dicot leaf cells and developed into a simple leaf-disc transformation system in which gene transfer, selection and regeneration are coupled together in an efficient process (50). Tobacco is an excellent host for Agrobacterium. It responds very well in in vitro culture and was the first plant species transformed using Agrobacterium. Advances in tissue-culture regeneration techniques and effective interaction with *A. tumefaciens* have provided a reproducible method for transfer of cloned, engineered genes in many dicot crop species including tomato, lettuce, sunflower, rape, cotton, and soybean (51). Recently, Agrobacterium-mediated transformation of so-called non-host crop plants has been accomplished in maize and rice (49, 52).

There are a number of technical issues that have required attention in the application of this technique to species other than model species (e.g. tobacco). One problem is inefficiency or ineffectiveness of the selectable marker. Escapes or false positives often occur, perhaps due to loss of DNA during plant development or due to the cross-protection of wild-type cells by nearby transformed cells. This problem generally has been solved by applying selection during more susceptible growth stages or using dual selection. Some plant species or genotypes respond differently to the same selection agent even though they are transformed with the same marker gene. Therefore, new marker genes and selection agents have been developed to use in those crops. Another problem has been the interaction between Agrobacterium and the explant, sometimes limiting the survival or vigor of the explants which, in turn, reduces the overall transformation efficiency. The strain of Agrobacterium can have significant impact on the efficiency of transformation (71).

Cellular competency for transformation and regeneration remains a major barrier for application of this procedure. One example is the sugar beet (*Beta vulgaris* L.). Early attempts to transform sugar beet based on Agrobacterium-mediated gene transfer demonstrated that cells are readily susceptible to transformation. However, the transgenic calli obtained were non-regenerable (62) or the recovery frequency of transgenic plants was very low (33). Recently, Hall et al. (40) reported a high-efficiency transgenic sugar beet system using stomatal guard cell protoplasts. He used computer-assisted microscopy that identified guard cells as the only progenitor or totipotent protoplasts in sugar beet leaves. This regenerable guard cell line could be a good candidate for Agrobacterium-mediated transformation. However, a non-uniform regeneration response was observed from initial cultures derived from guard cells, making this system unpredictable.

Particle Bombardment

Microprojectile bombardment, a transformation procedure, employs high velocity metal particles coated with DNA to deliver genes directly into cells. It can apply to a wide spectrum of experimental systems including plants, insects, fish and mammals (113). In plants, the concept has been described by Sanford (89) following the original observation by Klein et al. (59) that tungsten particles could be used to introduce macromolecules such as DNA and RNA into epidermal cells of onion with subsequent transient expression of the enzymes encoded by the DNA. Christou et al. (18) then demonstrated that the process could be used to deliver foreign genes into plant cells and stably integrate them into the genome. Particle bombardment is a direct method which can target any organ or tissue with single or multiple genes. Theoretically, it can be a genotype-independent transformation procedure if the targeted plant cells are totipotent. It limits or eliminates the time that the transformed cell line remains in tissue culture and thus reduces the risk of losing fertility due to tissue-culture-induced somaclonal variation. An efficient particle bombardment system for crops after the optimization of physical parameters requires target cells that are competent for both stable DNA integration and regeneration. Many crop species that are poor hosts for Agrobacterium and not efficiently transformed through protoplast-based procedures are candidates for particle bombardment. Fertile transgenic plants have been successfully obtained from crops that cannot be achieved by any other method, including wheat (108, 109). However, transformation frequency remains extremely low and only a few genotypes can be manipulated.

Viral Vectors for Gene Expression

The development of plant viruses as vectors to deliver foreign genes into plant cells has become an attractive tool to complement the currently available methodology (91), although it too has significant limitations. The decision to employ plant virus vectors over traditional plant breeding or transformation depends upon the goals of the application, as well as upon technical feasibility.

The potential advantages of using viral vectors include speed, flexibility of application, high levels of gene expression, and non-transmissibility through seed generations. Numerous plants of the same genotype or different genotypes of the same species can be infected with a virus to evaluate expression of a foreign gene. In addition, viruses carrying different genes of interest can be used singly or in combination, applied at the needed time to combat a specific problem or set of problems. Because of the nature of virus infection, the maximum level of foreign gene expression is predicted to occur within a brief period, usually within one or two weeks after inoculation. Another practical advantage is that many plant viruses are easily transmissible and potentially could be used for rapid mechanical inoculation of large acreages of crop plants. Also, once a suitable transient gene vector is identified, the expression of large numbers of genes can be tested rapidly in a variety of different plants that are hosts for the virus. As most viruses are not transmitted through the host germ line, the potential for environmental escape of foreign genes is limited.

Both DNA and RNA viruses have the potential to be effective vectors for gene delivery. It was generally believed that all plant viruses were RNA viruses until Shepherd (95) reported the cauliflower mosaic virus (CaMV) contains a double-stranded DNA genome. Cloned CaMV DNA was observed to be infectious when plants were mechanically inoculated (95, 96). This report resulted in an explosion of research on this and other plant virus systems. The CaMV 35S promoter has been used extensively as a promoter for constitutive expression of foreign genes. Today, the reverse transcription of viral RNA into cDNA that can be inserted into plasmid vectors for molecular cloning (3) and the in vitro transcription systems that facilitate the synthesis of infectious RNA transcripts from full-length cDNA clones (12) make feasible the use of RNA viruses as potential vectors.

Many strategies have been used to develop virus-based gene-delivery vectors. The main criterion for effectiveness of viral gene manipulation has been lack of disruption of essential viral functions. Strategies include gene replacement, gene insertion, complementation and artificial virions (91, 114).

Gene replacement. To reduce the possible detrimental effects of increased genome size when introducing a foreign gene into the viral genome, it has been proposed that viral genes be replaced by foreign genes. Many viruses have been tested as vectors for foreign gene expression using gene replacement, including CaMV, tobacco mosaic virus (TMV), potato virus X (PVX), tomato golden mosaic virus (TGMV), and African cassava mosaic virus (ACMV). For CaMV, mainly small genes have been replaced and expressed. The molecular recombination caused by rapid deletion of foreign inserts has limited its gene-vector potential (13). TMV, a single-stranded, plus-sense, rod-shaped RNA virus, theoretically can overcome paclaging constraints imposed by spherical virus coat proteins and could be more flexible and stable for expression of a foreign gene. When chloramphenicol acetyltransferase (CAT) replaced the TMV coat protein, high levels of expression failed to spread efficiently throughout the plant, because the coat protein is required for efficient long distance movement (21). This also occurred with PVX when the β-glucuronidase (GUS) gene was substituted (16). Replacement of the coat protein gene of TGMV and ACMV, both single-stranded DNA geminiviruses, resulted in vectors replicated and spread throughout infected plants, with concomitant high levels of foreign gene expression. Even though the DNA was not encapsidated, it appears that unknown structural features dictated that vectors were stable when their size was comparable to that of the wild type genome (44, 101).

Gene insertion. Gene replacement may affect the expression of the normal viral gene. To avoid such potentially negative effects, gene insertion or addition has been tested using several viruses, including TMV, maize streak virus (MSV), PVX, and tobacco etch virus (TEV). Duplication of a homologous coat protein subgenomic promoter has been shown to be a useful approach for the expression of foreign genes from PVX in whole plants. Insertion of the GUS gene downstream of the duplicated promoter sequence resulted in stable, strong GUS expression throughout the plants. However, GUS deletions did occur over time (16). Using TMV, this approach resulted in homologous recombination and loss of the foreign insert (63). However reducing the sequence's relatedness decreased the frequency of recombination events between the two subgenomic promoters, thus providing a more stable vector (28). For MSV, a geminivirus, systemic infection requires all of the intact viral genes without interruption (93), although localized expression of a foreign gene was obtained when it was inserted in the intercistronic region. The expression strategy of potyviruses like TEV involves cis-regulated proteolytic polyprotein processing steps, and as a consequence, foreign genes could not be simply inserted between other viral genes. These genes could be expressed either through insertional fusion with existing genes or through inclusion of appropriate adjacent proteolytic cleavage sites that permitted efficient protein processing and release of the foreign gene product along with the essential viral products (27). Although deletion events did eventually occur, the TEV vector was sufficiently stable to maintain GUS gene expression for several mechanical passages through plants.

Complementation systems. In the examples mentioned above, foreign genes are expressed from autonomously replicating viruses that have the potential to invade the plant systematically. Although these strategies have obvious advantages, limitations are imposed by the fact that most replacements of viral genes affect essential function, whereas gene insertion increases the genome size which may impact the ability to be packaged. To overcome some of these problems, helper-dependent systems have been explored in which foreign genes are inserted into defective viral components that either depend on transgenically introduced viral genes or on co-infection with a helper virus for essential function. The potential of this strategy has not yet been fully explored, but the feasibility of transgenic complementation of viral function has been demonstrated for a number of virus systems (25, 35, 107). This complementation approach could possibly be exploited for gene replacement strategies.

Artificial virions. A completely different approach to using plant viruses and their natural vectors for delivery of foreign genes to plants is that described by Zhang et al. (114). *Opidium brassicae* is a primitive zoosporic fungus that vectors tobacco necrosis virus (TNV) and several other viruses to numerous monocot and dicot species. A recombinant plasmid containing the CAT gene was encapsidated with the dissociated coat protein of TNV. Zoospores of *O. brassicae* were able to acquire these "pseudovirions" and transmit them to wheat roots. Two days after inoculation, expression of CAT could be detected in infected roots. The fate of the encapsidated plasmid in infected cells was not discussed. The authors indicated that this system might "provide an alternative" to "agro-infection" and particle-gun systems.

Limitations of Current Gene Delivery Systems

All of the above processes are highly technical, expensive, lengthy and difficult to control. The situation is often complicated by the incompetency or special requirements for competency of specific plant genotypes. Other important difficulties related to available transformation methods are poor expression of transgenes, loss or inactivation of transgenes and low regeneration frequency in some species or genotypes. Expression may be hampered by position effect or problems involving copy number (19, 20). Expression may be optimized through selection and screening of numerous independent transformants, though this is laborious and time consuming (100). Loss or inactivation of transgenes is frequently related to tissue-culture-generated somaclonal variation (65). Significant progress has been made in developing improved regeneration frequency, though this has occurred through empirical approaches that continue to defy a general understanding of genotypic variation in regeneration frequency (65). In addition to these difficulties, once seed containing a foreign gene is released, the gene can be transmitted to subsequent generations, so that control of proprietary genes requires substantial resources. In addition, effective use of transgenic crops may be limited since many crops can cross pollinate with their weedy relatives. Thus, the potential exists for transfer of foreign genes into these weed species, with undesirable environmental consequences.

The use of plant viruses as vectors of foreign genes has numerous advantages over more traditional methods of introducing genes into plants; however, there are certain problems associated with the use of plant virus vectors that could potentially minimize their usefulness. There are technical difficulties related to packaging, stability and expression, and agricultural-application problems related to containment and host specificity of the virus vector and associated foreign genes to the targeted host species.

Rapid recombination of the modified virus appears to be the predominant cause of instability and deletion of foreign genes (99). Instability problems are more prevalent when large genes are inserted rather than small genes (91). The mechanism responsible for deletion is unclear, however, the ability of viruses to delete foreign inserts may reflect a universal strategy that has evolved to protect viruses against promiscuous incorporation of host genes and subsequent amplification of non-advantageous sequences. Since many unknown and currently unpredictable factors may contribute to instability, it is important to test the effects of a variety of gene insertion sites and strategies in exploring the use of any virus as the vector of foreign genes. Other technical limitations to the use of viral-based vectors include the usually brief period of maximum expression, and poor understanding of host delivery and movement mechanisms.

By definition, plant viruses are pathogens and are capable of causing disease and reducing yields in infected plants. Rhizomania, "root madness" is a severe disease of sugar beet caused by beet necrotic yellow vein virus (BNYVV) and transmitted by the soilborne fungus *Poymyxa betae*. The disease is widely distributed in many countries and is economically devastating to a sugar beet crop, causing severe loss in root yield and sugar content of the infected plants. In naturally infected plants, BNYVV is normally confined to the roots, and causes massive proliferation of the lateral rootlets of taproots as well as other abnormalities of the root system.

Although some virus vectors have been genetically modified to reduce the virulence of plant viruses (91) most have not. Furthermore, many of the viruses used as vectors have extremely wide host ranges and infect both monocots and dicots (91). Even if a naturally mild virus isolate is intended for use as a vector with a specific host, it could potentially be virulent to a non-target species. Fear that an introduced virus might move from the intended target plant to a non-target host is one reason cross protection has not been widely adopted as a means of biological control of plant virus diseases (34, 86, 96). The possibility that a recombinant virus could escape into the environment and introduce a foreign gene into a non-target species constitutes an even greater constraint to the development and use of virus-vector-delivery systems in production agriculture. Viruses that have large host ranges and are easily transmitted mechanically or by insects can be subjected to extreme scrutiny from regulatory agencies and the public. Even though there are certain advantages to selecting viruses with large host ranges as virus vectors, regulatory concerns may dictate the development of systems with vectors that are more host specific. Such a mandate would be in line with the shift in pesticide use that has occurred over the last ten years, from broad spectrum pesticides to those with more specific modes of action.

Novel isolates of beet soilborne mosaic virus, BSBMV (previously called Texas 7), have now been identified as non-virulent or mildly virulent viruses closely related to BNYVV. When co-inoculated with BNYV in a susceptible host, BSBMV dominates over BNYVV, and interferes with infection by the more pathogenic BNYVV. A method for preferentially incorporating BSBMV into plants and thereby excluding or inhibiting infection and disease caused by the more virulent BNYVV would be extremely useful, especially in the sugar beet industry. Such a method would also be of great utility for inoculation of plants against a variety of severe diseases caused by furoviruses.

Similarly, a method for easily incorporating a competing, non-virulent or mildly virulent virus into a plant to confer protection against a more virulent pathogen would be highly desirable. Such a method should be easily applied in the field, permit specific application to a plant or field of choice, and be stable over time. The methods of the present invention provide such easily administered and controlled application of a beneficial virus or other desired nucleic acid sequence to a host plant.

In addition, the methods of the present invention describe a novel gene delivery system that uses the natural fungal vector and a seed coating treatment. The invention method results in products specific to the crop of interest and the trait (or set of traits) of interest. It can be applied quickly and easily by the grower without the need for specific training. Further, since the gene(s) is (are) not incorporated into the plant's genome, and is therefore not genetically transmissible, the manufacturer is in an excellent position to control the release and distribution of the product(s). Owing to the obligate nature of the relationship among host plant, fungal vector and virus, opportunities for unintended transmission of gene is minimal.

In addition, the methods of the present invention relate to the delivery of recombinant or wildtype viruses to cells via the infection of plants by soilborne fungi containing wildtype or recombinant viruses.

The development of a seed treatment system for viral delivery as well as virus-mediated gene delivery to plants is a novel concept which fits well with the goal of achieving sustainability of U.S. agriculture. It will improve productivity by increasing crop quality, and value, which, in turn, will improve the economic viability of farm operations. Also, such a system could potentially enhance environmental quality by, for example introducing resistance genes into plants which could reduce requirements to pesticide use.

SUMMARY OF THE INVENTION

The invention details the use of viruliferous fungal survival structures, applied as a seed coating, to deliver a virus of interest.

In one embodiment, soilborne fungi can be used to deliver viruses to a plant. As an example of the delivery of virus to plans, in one preferred embodiment, a mildly virulent or non-virulent virus is selectively administered to plants for purposes of reducing or eliminating infection by or disease development caused by a more virulent pathogen. The mildly-virulent or non-virulent virus is transmitted to the plant through a soilborne fungus which is permitted to contact and thereby infest plant seed. Plant seed coated with the viruliferous fungus is stable for long periods of time. When the coated seed is planted in soil, the growing plant becomes infected by the viruliferous fungus which transmits the mildly-virulent or non-virulent virus to the plant. The mildly-virulent or non-virulent virus interferes with the expression of disease symptoms by a more-virulent virus which might otherwise infect the plant, thereby protecting the plant from severe disease.

In another preferred embodiment, the inventive method is used to prevent, delay or reduce BNYVV mediated disease development in sugar beet plants. In a most preferred embodiment, the mildly virulent protective virus is BSBMV.

A soilborne fungus, e.g., Polymyxa which transmits BNYVV, BSBMV, and BSBV, and numerous other furoviruses, is first infected with a mildly virulent or non-virulent virus, and the viruliferous fungus is then coated onto seed. Most preferably, the seed is coated with a composition containing the viruliferous fungus or with the survival structures of the fungus (e.g., cystosori in Polymyxa) prior to planting the seed in soil. The seed coating composition preferably consists of dried, powdered roots of a plant infected with a viruliferous soilbome fungus or cystosori of viruliferous fungus, the fungus being infected with the mildly virulent or non-virulent viral isolate.

This invention also details a virus-based gene delivery system that can be applied as a seed treatment for plants. Specifically, in addition to vectoring viruses into plants, this invention also details a novel means of introducing foreign genes into plant cells in planta, via a seed treatment that uses recombinant furoviruses and their natural fungal vectors. In this embodiment, viruliferous fungus coating on seeds is used as a vector means for delivering foreign genes or recombinant viruses into plants to enhance agronomic traits, and the production of desirable products such as pharmaceuticals. This inventive delivery system possesses the following important features: 1) ease of application (seed coating), 2) longevity of the seed treatment product, 3) minimal risk of transmission to subsequent seed generations, 4) specificity of the delivery system to only a few species and 5) universality of the delivery system with a species.

The invention foreign gene/viral transfer technique takes advantage of a seed coating treatment recently developed in which viruliferous *P. betae*, applied as a seed coating to sugar beet seed, is able to infect germinating seedlings and inoculate the seedling with BSBMV (41). This invention method adapts this system to deliver a recombinant isolate of BSBMV or any other recombinant furovirus to selected hosts. This technique is inexpensive and easy to apply, potentially to every plant in the field. Because the treatment remains viable for long periods of time, the invention method enables seeds treated with recombinant vectors to be stored, at least until planting time. Importantly, because of the host/vector specificities, the invention method greatly reduces the chances of the recombinant virus escaping into the environment.

DETAILED DESCRIPTION OF INVENTION

In one example of the delivery of viruses to plants a mildly virulent or non-virulent virus is transmitted to a plant to confer tolerance or resistance to a more virulent viral pathogen. Such protection or interference is conferred by viruses having sufficient similarity and characteristics as the normal virulent virus to be recognized and accepted by the host, yet having less virulent pathogenic characteristics so as to lessen or preclude the disease caused by the virulent virus. For example, BSBMV has much similarity in structure and function to BNYVV, but do not induce the severe symptoms of Rhizomania in plants that are induced by BNYVV.

Mildly Virulent Pathogens

To be useful in the present method invention, a non-virulent or mildly virulent virus is a strain or isolate of a virus, preferably a virus transmitted by a soil fungus, e.g., a furovirus, which shares substrate specificity, binding and functional characteristics with a more virulent strain of a pathogenic virus yet, unlike the pathogenic virus, fails to induce severe disease symptoms in plants. The mildly virulent or non-virulent isolate must also dominate over or interfere with symptom expression of a more virulent, disease-causing virus in a plant susceptible to both viruses, such that infection of a plant by the mildly or non-virulent virus precludes survival and/or effectiveness of the more virulent virus in causing disease in the plant.

To test a sample isolate or strain for utility as a mildly or non-virulent virus in the method of the instant invention, a test virus is directly (e.g., mechanically) inoculated into a plant, preferably alongside mock-inoculated and virulent pathogenic virus-inoculated plant controls. As compared with the virulent virus-inoculated control plant, a mildly or non-virulent virus useful in the present invention will not induce severe disease symptoms in the plant. It is recognized, however, that a mildly-virulent virus may induce some mild disease symptoms, but this does not preclude its utility in the method invention. This is especially true in plant diseases such as Rhizomania, where the virulent virus causes such devastation to sugar beet plants that induction of mild disease symptoms is desirable to prevent great crop loss through the severe disease caused by the virulent pathogen.

The mildly virulent or non-virulent virus must also dominate over the more virulent virus, and inhibit infection or interfere with symptom expression of the more virulent virus in the host plant. To test for this characteristic, a plant is co-inoculated with both the mildly or non-virulent virus (protecting virus) and the more virulent virus, or the plant is first inoculated with the protecting virus, followed by inoculation with the virulent virus. After a period of time to permit virus to infect the plant's system, the plant is assayed for the systemic presence of each virus, e.g., by ELISA.

Alternatively or in combination with the above, the co-inoculated plants are observed for expression of disease symptoms characteristic of the pathogens. To be useful in the present invention, the mildly or non-virulent virus will dominate, or interfere with phenotypic expression or pathogenic disease symptoms of the virulent virus, that is, the disease symptoms caused by the non- or mildly virulent virus are seen in the co-infected plant, and not the severe disease symptoms caused by the more virulent virus.

Representative examples of these assay procedures are found in the Examples described below, which demonstrate the similarities of BSBMV viral isolates to the virulent pathogenic virus BNYVV, known to cause Rhizomania in sugar beet plants. BSBMV is demonstrated to be mildly virulent as compared with BNYVV, causing only mild disease symptoms in plants rather than more severe disease symptoms caused by BNYVV, and show dominance in symptom phenotype over BNYVV when co-inoculated into plants.

BSBMV isolates (also known as Texas 7) are natural virus isolates, found, for example in soil samples from Texas sugar beet-growing counties. See, for example (45). Several BSBMV isolates found in Texas, Nebraska, and California are described in Table 1. These isolates, obtained from plant or soil samples, each tested positive for BSBMV and negative for BNYVV by ELISA and by RT-PCR assay. An example of BSBMV is BSBMV, on deposit at the American Type Culture Collection and having ATCC Accession No. 75883 BSBMV isolates confer tolerance to disease caused by BNYVV.

TABLE I

| | | | | RT-PCR PRODUCTS[b] | | |
|---|---|---|---|---|---|---|
| | | SYMPTOMS[a] | | BNYVV | BSBMV | Tha I |
| Isolate | Origin | Sugar Beet | *C. quinoa* | Primers | Primers | Cleavage |
| BNYVV | Calif. | NFS, RB | YS | 1056 | None | No |
| BSBMV-Neb gfs | Neb. | NRS, SDYB | DCS | 1000 | 700 | Yes |
| BSBMV Neb gh | Neb. | NRS, SDYB | YS | 1000 | 700 | Yes |
| BSBMV- | Neb | NRS, | YS | 1000 | 700 | Yes |

TABLE I-continued

| | | SYMPTOMS[a] | | RT-PCR PRODUCTS[b] | | |
| | | | | BNYVV | BSBMV | Tha I |
| Isolate | Origin | Sugar Beet | C. quinoa | Primers | Primers | Cleavage |
| --- | --- | --- | --- | --- | --- | --- |
| Neb Morrill | | SDYB | | | | |
| BSBMV-Marken | Tex. | NRS, SDYB | DCS | 1000 | 700 | Yes |
| BSBMV-NC | Tex | NRS, SDYB | DCS | 1000 | 700 | Yes |
| BSBMV-FS | Tex. | NRS, SDYB | DCS | 1000 | 700 | Yes |

[a]Symptoms expressed on the sugar beet for which isolates were originally obtained or on mechanically infected Chenopodium quinoa;
NFS = no system is foliar symptoms;
NRS = no obvious root symptoms;
RB = root bearding;
SDYB = systemic diffuse yellow banding on leaves;
YS = yellow spots; and
DCS = diffuse chlorite spots
[b]Approximate size in base pairs as determined by reverse transcriptase polymerase chain reaction.

In a similar manner, plants may be made tolerant to other diseases caused by virus vectored soil borne fungus. Examples of such plant diseases caused by the pathogenic viruses are listed in Table 10.2 of *Plant Virology,* 3rd Edition, Ref. Matthews, ed., Academic Press, NV, 1991, p. 346.

Soilborne Fungus

In the present invention, a soilborne fungus is used to transmit the virus to a host plant. Several types of soilborne fungi are known which vector various pathogenic viruses to host plants. For example, Polymyxa, known to vector BNYVV, has now been found to vector BSBMV, a mildly virulent virus which interferes with BNYVV disease expression in co-inoculated plants, as well as BSBV.

Polymyxa is a member of the family Plasmodiophoraceae and is a ubiquitous soil inhabitant that lives as an obligate parasite on plant roots. The fungus multiplies only within the roots of a host plant. During this multiplicative phase, a plasmodium is formed within the plant cell and can become viruliferous when the host is infected with a virus, i.e., furovirus. The infected plasmodium then differentiates into either a zoosporangium giving rise to new zoospores, or thick-walled resting spores called cystosori. Cystosori, which are released into soil as roots senecse and die, permit the fungus and its infecting virus to survive without a host for long periods of time in the released cystosori.

There are two known species of Polymyxa: *P. betae* Keskin and *P. graminis* Ledingham. *P. betae* colonizes plants of the families Chenopodiaceae, Anaranthaceae, and Portulacaceae. *P. graminis* colonizes many grasses. There are at least twelve separate viruses in two taxonomic groups known to be vectored or carried and transmitted into plants by Polymyxa species, including BNYVV by *P. betas* and peanut clump virus (PCV) and wheat spindle streak mosaic virus (WSSMV) by *P. graminis*.

To be useful in production agriculture, a virus vector gene delivery system needs to be easy to use, inexpensive, effective, and environmentally safe. A recently developed method of inoculating sugar beets with BNYVV has tremendous potential for use in such a system (41). Dried roots containing cystosori of viruliferous *P. betae* can be used to coat seed and this method is currently used extensively in our research for field and greenhouse studies (42,46,68). A patent of this technology as a biological seed treatment for control of specific furovirus diseases has been allowed (U.S. patent application Ser. No. 08/299,608) and is incorporated herein by reference. This technique of inoculating plants with a furovirus is easily modified to package and deliver recombinant BSBMV transformed with a gene or genes of choice. Theoretically, this system could be used with any mild furovirus vectored by Polymyxa spp. Because of this and other reasons outlined below, we believe that BSBMV and its fungal vector *P. betas* are logical candidates for development of a model seed treatment system for delivery of foreign genes to plants with virus vectors. In order to gain a better understanding of this invention, a background of the furoviruses and their fungal partners is provided below Furoviruses Based on the criterion of limited host range, the genus Furovirus has several members useful as vectors. Furoviruses are fungal-transmitted, rod-shaped viruses with divided genomes (14, 15, 78). The name was first proposed by Shirako and Brakke (98) in 1984 and accepted by the International Committee on the Taxonomy of Viruses (ICTV) in 1987 (31). These viruses occur in temperate regions of five continents, and several of the most important members of the group have wide geographical distributions (15). The natural fungal vectors of these viruses belong to the genera Polymyxa and Spongospora (2, 36). Polymyxa spp. are soil inhabitants and survive from year to year as tightly compacted survival structures called cystosori. Cystosori are extremely resistant to environmental degradation and furoviruses can remain viable within these structures for years without loss of virulence (1). In the presence of a host and proper environmental conditions, cystosori give rise to zoospores. Zoospores swim through free soil water until they contact a host root and encyst. Cytoplasm from the encysted zoospore enters the infected root cell and if the zoospore is viruliferous, the virus can be transmitted to the infected cell (73). The effect of root infection by aviruliferous Polymyxa spp. is minimal (37, 74).

Soilborne wheat mosaic virus (SBWMV) is the type member of the Furovirus. Other members include beet necrotic yellow vein virus (BNYVV), peanut clump virus (PCV), oat golden stripe virus (OGSV), potato mop top virus (PMTV), and rice stripe necrosis virus (RSNV) (15, 31), broad bean necrosis virus (BBNV), fern mottle virus (FMV), Hyposhoeris mosaic virus (HMV), Indian peanut dump virus (IPCV), Nicotiana velutina mosaic virus (NVMV). Recently, sorghum chlorotic spot virus (SCSV) and beet soil borne mosaic virus (BSBMV) have been tentatively identified by ICTV as furoviruses (45,110). Several reviews have been written on the biology of this genus (14,15,78,83).

As suggested by their names, furoviruses infect a wide range of economically important crops. They cause serious disease of several economically important crops, thus their control is of great importance (14).

Most individual members of the group, however, have fairly restricted host ranges. Host ranges of the fungal vectors, Polymyxa spp. are also quite limited (2,4,5,6,38). The limited host ranges of most furoviruses and their fungal vectors suggests that these viruses might be ideally suited as virus vectors for use in large scale agricultural production systems. Furthermore, studies of BNYVV conducted by Jupin et al. have proven that furoviruses are amenable to gene replacement (57).

Beet necrotic yellow vein virus is a plus-sense RNA furovirus with a quadripartite genome (9,10,11,78,104). RNAs 1 and 2 are essential for viral replication and RNAs 3 and 4 are required for symptom expression and transmission by the fungal vector, P. betae (8,54,66,78,102). Infectious transcripts of all four RNA species have been synthesized and used to study gene function by examining the biological properties of RNA molecules containing deletions introduced at the cDNA level (55,75,77,114). In a study of cis-active features on BNYVV RNA 3, Jupin et al. (55) found that up to 75% of the central core of RNA 3 transcripts could be deleted without affecting amplification or encapsidation. The deleted region was replaced with the β-glucuronidase (GUS) gene and GUS activity could then be detected in infected tissue. This study demonstrated that in the presence of RNAs 1 and 2, the 5' and 3' cis-regulatory domains of BNYVV RNA 3 were sufficient to drive the amplification and expression of a foreign gene in infected tissue.

Beet soil borne mosaic virus. Although BNYVV could be used as a vector of foreign genes, the fact that it is extremely virulent eliminates it from consideration for use in production agriculture. RNA 3 deletion mutants of BNYVV exhibit reduced disease symptoms (56,60,61,64,102,103), but the potential for recombination with wild-type populations in a field situation presents too great a risk. Beet soil borne mosaic virus (BSBMV), which is similar to BNYVV but only weakly pathogenic (46,68), may be an acceptable alternative (Table 2).

TABLE 2

Similarities between BSBMV and BNYVV[a]

1. Host range
2. Vectored by P. betae
3. Quadripartite genome with 3' polyadenylation
4. Weak serological relationship
5. Molecular weight of capsid protein-approximately 22 kDa
6. Nucleotide sequence and genomic organization

[a]Data excerpted from Heidel et al. (48, 49); Wisler et al. (110)

BSBMV was discovered in Texas in 1985 (29) and now has been identified in California, Colorado, Idaho, Minnesota, Nebraska, and Wyoming (45,67). Beet soil borne mosaic virus and BNYVV are differentiated from other furoviruses in that both have quadripartite, polyadenylated genomes. This and the other similarities between BSBMV and BNYVV (Table 2) prompted Rush et al. to speculate that BSBMV was a mild strain of BNYVV (79,80,81,84). However, they also warned that additional work was required to determine the true taxonomic relationship between the two viruses.

In an early attempt to develop a diagnostic test that could accurately differentiate BSBMV from BNYVV, it was discovered that primer pairs derived from published nudeotide sequences of BNYVV RNAs 1–4 (8,9,10,11) amplified rt-PCR products when BSBMV cDNA was used as template (82). Furthermore, when these BSBMV rt-PCR products were digested with restriction endonucleases, RFLP patterns were similar to those predicted for BNYVV, indicating a high degree of nucleotide sequence similarity. Recently, rt-PCR products from BSBMV RNAs 1–3 have been sequenced. Approximately one-half of RNAs 1 and 3 have been sequenced and all of RNA 2 (4,546 nt) has been cloned and sequenced except the terminal 5' nucleotides (85). When sequence data from BSBMV RNAs 1–3 were entered into the BLAST program, best fit in every case was with BNYVV. Computer assisted analysis of potential coding capacity of BSBMV RNA 2 sequence indicated further similarities with BNYVV RNA 2. Six putative open reading frames (ORFs) of similar size and position to those of BNYVV RNA 2 were identified. Coordinates of the putative ORFs of BSBMV RNA 2 and estimates of their translation products are shown in Table 3.

TABLE 3

Predicted coordinates of BSBMV-FS RNA2 ORFs (85)

| ORF | First AUG (nt) | Termination (nt) | Protein (Mr) |
| --- | --- | --- | --- |
| 1 | 53 | 628 | 20,953 |
| 2 | 53 | 1,863 | 75,580* |
| 3 | 2,110 | 3,180 | 38,990** |
| 4 | 3,180 | 3,536 | 12,602 |
| 5 | 3,520 | 3,918 | 14,660 |
| 6 | 3,946 | 4,308 | 13,719 |

*Assuming readthrough of ORF 1
**Modification of ORF 3 by elimination of one nucleotide (nt) in the BSBMV-FS sequence increases the size of the predicted protein to approximately 42,000 daltons, the same as ORF3 of BNYVV RNA2.

The first ORF begins at nucleotide (nt) 53 and ends with an UAG at nt 628, to give a protein of 20,953 daltons. Following the stop at nt 628, an in-phase coding region extends to nt 1863 to encode a predicted readthrough translation product of 75,580 daltons. These first two ORFs are analogous to the coat protein region and readthrough of BNYVV and have been detected in protein blots using antiserum developed against BSBMV coat protein (48,85). The remaining four ORFs of BSBMV RNA 2 are also similar in size and position to those on BNYVV RNA 2.

BLAST analysis of putative BSBMV RNA 2 ORFs showed greater amino acid sequence homology with BNYVV than with several other related viruses. The highest degree of homology was in ORF 4, which exhibited 81% identity and 90% similarity. The least homology was in ORF 6, which codes for a 14 kDa non-structural protein in BNYVV and had only 40% amino acid sequence identity with the analogous region in BSBMV. The coat protein region of BSBMV and BNYVV had 59% identity and 72% similarity. All ORFs of BSBMV had regions which exhibited greater than 90% amino acid sequence homology with analogous ORFs of BNYVV. When amino acid sequences from specific ORFs of BNYVV were compared by best-fit analysis to BSBMV and several other related viruses, BNYVV was more similar to BSBMV than to any of the other viruses (Table 4). An additional and interesting similarity between BSBMV and BNYVV RNA 2 is that one isolate of BSBMV, designated BSBMV EA, has a deletion of approximately 500 nt. Deletions of similar size have been observed in RNA 2 of BNYVV (10).

TABLE 4

Best fit comparisons between specific BNYVV ORF regions and comparative regions of several related viruses (85)

| BNYVV | 21 kDa | 42 kDa | 13 kDa | 15 kDa |
|---|---|---|---|---|
| BSBMV | 59(72)* | 74(86) | 81(90) | 65(78) |
| PCV | 18(40) | 30(51) | 32(51) | 20(44) |
| PMTV | 19(39) | 29(50) | 37(56) | 20(46) |
| NVMV | 21(42) | 26(53) | 40(62) | 23(49) |
| BSMV | 21(43) | 27(50) | 42(63) | 12(42) |
| BSBV | 14(34) | 29(50) | 39(56) | 23(47) |

*Values represent percent amino acid identity and similarity, respectively

These data could be used to either support or refute the speculation that BSBMV is a strain of BNYVV; however, since other identified strains of BNYVV differ from each other by only a few nucleotides, we conclude that BSBMV is distinct from BNYVV. We also conclude that the similarities between the two viruses warrant the creation of a sub-group within the genus Furovirus with BNYVV as the "type" member. Although BSBMV is now considered to be distinct from BNYVV, similarities between the two viruses are sufficient to allow the use of BNYVV as a "model" in molecular studies of BSBMV. The strategy of using BNYVV as a molecular model in our research of BSBMV has been remarkably successful, and all results to date support the hypothesis that BSBMV could be used successfully as a virus vector in a gene delivery system (48,82,85).

In a preferred embodiment of the invention, a mildly or non-virulent virus isolate is vectored or carried and transmitted to a plant by a soilborne fungus. The host plant must be susceptible to infection by the soilborne fungus and by the virus it carries. The fungus must be susceptible to infection by the mildly or non-virulent virus.

Screening of virus-fungus infection and fungus-host plant infection may be carried out by routine methods known to those of skill in the art. In general, a plant previously artificially inoculated (e.g., by mechanical methods) with a virus is permitted to grow in soil known to contain the specific soilborne fungus to be tested. After permitting the fungus to colonize the roots of the infected plants, the fungus is harvested and analyzed for the presence of the virus, e.g., by directly analyzing the fungal cystosori for the presence of the virus using PCR amplification and hybridization techniques, or indirectly, e.g., by harvesting the cystosori, mixing them with clean soil, and planting in the soil uninfected plants. Fungus then is permitted to colonize the roots of the plants, and the plant is monitored for infection by the transmitted virus by ELISA or by manifestation of mild disease symptoms in the plant known to be induced by the virus.

Coating Seed With Viruliferous Fungus

In a preferred embodiment of the invention, seed of a plant susceptible to a virulent pathogenic virus transmitted by soilborne fungus is coated with a composition containing a viruliferous fungus. The fungus may be infected with a mildly-virulent or non-virulent virus that is recombinant or wildtype. The seed-coating composition contains viruliferous fungus either in the form of fungal resting structures, i.e., cystosori or as infected root material.

Preferably, the cystosori or infected root material is dried, the roots are generally pulverized to powder form. An aqueous slurry of the fungal material is prepared by placing the dried, pulverized fungus material in a solution containing a polymer such as methyl cellulose (e.g., about 0.5–10% by weight). The polymer causes the fungus composition to be "sticky" and to adhere to the seed.

Seed is added to the aqueous slurry of fungal material and mixed until seed is coated. Generally, the slurry is sufficiently fluid to coat the seed on mixing. The coated seed is spread on a surface and permitted to air dry or dried under heat, e.g., in drying ovens. When dry, the seed has an adherent viruliferous fungal coat which is stable upon typical seed storage conditions.

The amount of viruliferous fungus adhered on the seed will vary with the amounts of reagents contained in the slurry. As few as 50–75 seeds may be coated with as much as 400–500 mg of the fungal material. This provides a great advantage for first infecting a growing plant with a desired non-or mildly-virulent virus to inhibit or induce tolerance or subsequent infection by a more virulent virus which may be present in the soil.

The inoculum on seeds remains functional for as long as, for example, the cystosori are viable. Studies have shown seed treated approximately two years prior to planting contained infectious inoculum (41).

Transmission of Foreign Nucleic Acids

To date, the technology has been used in epidemiological studies of viruses with fungal vectors, and also in cross protection studies. The novel and unique aspect of the seed treatment system of the present invention is the addition of a foreign gene to the virus for transient expression in the infected plant with delivery of the recombinant virus to a specific host achieved as previously described. In this case, however, the virus is not simply a mild version of a virulent plant virus, but rather it is a recombinant virus containing a foreign gene or genes of interest. Thus, in addition to the possibility of protection against a specific disease, a variety of other agronomically beneficial traits can be introduced.

In a preferred embodiment of the present invention, the method of seed-coating with a viruliferous fungus provides an effective and stable method for transmitting a nucleic acid of choice to a host plant. A viruliferous fungus infected with a virus which carries the nucleic acid of choice is coated onto seed of the host plant as described above for a mildly- or non-virulent virus. During growth of the seed into a plant, the viruliferous fungus infects the plant and transmits the virus and the nucleic acid of choice to the plant for systemic expression.

Plants are screened by methods known to those of skill in the art for expression of the inserted nucleic acid sequence, e.g., by ELISA.

In another embodiment of the invention method, the recombinant virus itself, rather than the specific gene or genes it carries, is the goal of the seed coating treatment. That is, the seed coating treatment can be used to deliver both foreign genes and foreign viruses of interest to plant cells.

There are many additional advantages of this inventive system over the currently known methods of gene transfer to plants. The viruliferous fungal survival structures which contain the recombinant virus can be sold to seed treatment companies or specific formulations can be developed as a hopper box treatment for on farm application. Likewise, this viruliferous seed treatment can be used in greenhouse applications or anywhere that introduction of foreign genes into a specific plant is desired.

Because the foreign gene introduction is accomplished via a seed treatment, it is much cheaper and more applicable than any other means of gene insertion. The ability of the fungal vectors to survive in the overwintering survival structures of their hosts means that the seed treatment can be prepared and stored until needed without losing its activity. Furthermore, this system is more environmentally acceptable than other virus vector systems due to the limited host range of the virus and its fungal vector; it is nearly impossible for the foreign gene to escape into the environment. In contrast to other systems, gene delivery by the invention method can be targeted specifically to the roots of the target plant or tailor-made for systemic movement throughout the plant. In addition, owing to the size and quadripartite organization of the furovirus genome, this technique permits the delivery of several different genes at once.

To illustrate the invention method, a modified version of BSBMV carrying a marker gene, is vectored by *P. betae* into *Beta Pulgans* var. *maritima*, a relative of common sugar beet (*B. vulgaris* var. *vulgaris*). The following outlines experiments that can accomplish this goal: (1) Construction of full-length cDNA clones of BSBMV RNA 2 and 3 which contain the marker gene, (2) synthesis of full-length infectious BSBMV RNA 2 and 3 transcripts from recombinant plasmids, (3) introduction of infectious RNA transcripts into *P. betae*, and (4) evaluation of the expression of the marker gene in *B. vulgaris* seedlings arising from seed treated with viruliferous *P. betae* cystosori.

The application of this system can be extended to other crop plants. This is possible due to the widespread existence of furoviruses with natural Polymyxa vectors that are amendable to seed coating crop hosts. *P. graminis*, for example, vectors soilborne wheat mosaic virus (SBWMV) into wheat and other small grains. As the world's most widely-grown crop and a species which has been recalcitrant to the application of other gene delivery systems, wheat would be a logical choice for extension of the system to be developed.

A technique has been developed in which viruliferous *P. betae*, applied as a seed coating to sugar beet seed, is able to infect germinating seedlings and inoculate the seedling with BSBMV (41).

In our laboratory, we have taken advantage of the many similarities between BNYVV and BSBMV, and used the results of previous studies of BNYVV as a blueprint for molecular studies of BSBMV. This strategy has been very successful.

Most studies of virus-mediated gene delivery have used mechanical inoculation to infect the host with the recombinant virus. Although these studies have been useful in testing general principles and feasibility, they have provided limited information regarding their potential for use in actual production systems. For virus-mediated gene delivery is to be commercialized and implemented at the farm level, it is imperative to determine how natural vectors of recombinant viruses affect gene expression and spread to non-target species. The present invention shows not only that furoviruses can be used as virus vectors, but also that the system can be expanded to include the natural fungal vector. High levels of foreign gene expression can be achieved after natural infection of host plants with viruliferous Polymyxa. Thus, the Polymyxa cystosori containing a recombinant furovirus can be used to develop a seed treatment virus-mediated gene delivery system that is inexpensive, easy to use, and environmentally safe.

Owing to the close relationship between BSBMV and BNYVV, detailed above, the development and modification of cDNA clones of BSBMV closely parallel methods previously used for BNYVV (10,11,55,75,90,92,224). We can utilize, as appropriate, other methods of generating full-length, infectious cDNA clones and synthetic transcripts (12,27,28,39,88,101). A brief outline of full-length clone construction is summarized below.

EXAMPLES

The present invention may be better understood by reference to the following examples, in which BSBMV is characterized as a mildly virulent viral isolate which dominates in co-cultures with BNYVV, is transmitted or vectored to host plants by the soilborne fungus *Polymyxa betae*, and confers to host plants resistance or tolerance to more virulent BNYVV infection, thereby protecting host plants from severe Rhizomania. The following are exemplary forms of the invention, are not intended to limit the scope of the invention.

Example 1

BNYVV Transmitted to Sugar Beet Plants by Coating Seed With Virus-Infected Soilborne Fungus Preparation of Viruliferous Fungus BNYVV-infected sugar beet plants were grown in Ray Leach Cone-Tainers (Stuewe and Sons, Inc., Corvallis, Oreg.). After 8–12 weeks in the greenhouse, randomly chosen plants were checked microscopically for infection by *P. betae* by looking for the characteristic cystosori of *P. betae* in infected roots under 10× magnification and assayed by enzyme-linked immunosorbent assay (ELISA) for BNYVV infection.

Roots from infected plants were thoroughly washed and allowed to air dry. The dried root tissue was pulverized and separated from soil and other foreign materials by a series of fine-meshed sieves. The resulting product consisted of powdered roots infected with viruliferous cystosori of *P. betae*.

Coating Seeds With Viruliferous Fungus

Seeds of sugar beet cultivar HH39 (Holly Hybrids, Sheridan, Wyo.) were coated with the powdered root material suspended in 2% methyl cellulose. Two batches of the seed-coating composition were prepared, the first having a ratio of 1:20:20 (w/v/w) of powdered root tissue/2% methyl cellulose/seed, and the second effectively doubling the amount of the powdered root tissue with the ratio being 1:10:10.

Seed was added to the suspension of root inoculum in methyl cellulose, mixed thoroughly, and allowed to air dry.

Growing Plants From Viruliferous-Fungus Coated Seed

Two to three seeds were planted in each container with a mixture of sand and commercial topsoil. Fifty containers were planted with the *P. betae*-BNYVV-coated seed (1:20:20 ratio) and fifty with control, untreated seed. The containers were kept in a greenhouse at ambient temperature (20–30° C.) and heavily watered for the first several weeks after planting to initiate early infection. After plants became established, they were watered daily to maintain plant turgor. One-half of the plants were harvested after approximately one month and plant tissue was assayed by ELISA for incidence of BNYVV infection. The remaining plants were harvested after approximately two months and assayed for BNYVV infection.

The greenhouse study was repeated using the seed-coating composition with the 1:10:10 ratio. Plants were harvested and analyzed for BNYVV at approximately four months after planting.

A field study was conducted in soil that had never before been planted with sugar beets. The test site consisted of two 9 m×30 m plots enclosed on all four sides by a border dike. Each plot contained eight beds with 76 cm spacing, with each bed considered one replication. A single row of untreated seed was planted on the four inside beds of each border. A rate of 15–20 seeds per meter was used to plant the HH39 sugar beet seed at a depth of 2 cm. The two outside beds on each side of the plot were sown in the same manner with the P. betae-BNYVV-coated seed (1:20:20 ratio).

The test field was irrigated the same day as planting, followed by three successive irrigations during the season. Irrigation was accomplished by quickly filling the furrows of the enclosed plots until the water reached to just below the top of the beds. The water was allowed time to soak into the beds, then plots were flooded once more. Each bed and furrow was blocked at the end so the irrigation water was contained within each furrow and not allowed access to an adjacent furrow or bed. Each irrigation added approximately 6–8 cm of water.

Analysis of growing plants for the presence of BNYVV was conducted twice during the season by the methods described for the greenhouse study. Ten samples were collected at 3 m intervals from each of the eight rows planted with BNYVV-coated seeds. Four to five beets were bulked from one location and constituted a sample. Two random samples were assayed from each of the eight control rows.

The field study was repeated using the seed-coating composition with the 1:10:10 ratio. All parameters were the same, except one less irrigation event. Only one field harvest and ELISA analysis was performed on these plants.

ELISA for BNYVV

The ELISA assays employed a double antibody sandwich technique using commercially available antisera and enzyme conjugates obtained from Bioreba Ag (Chapel Hill, N.C.) and Agdia (Elkhart, Ind.). Field and greenhouse samples were washed free of soil, and 0.25–0.30 g of root tissue was collected for assay. In addition to the test samples, each 96-well assay plate included four separate healthy control samples, four BNYVV-positive control samples, and four control buffer blanks.

Polyvinyl chloride (PCV) microtiter plates were coated with BNYVV Immunoglobin G (IgG) diluted per the manufacturer's recommendation in 0.1 M phosphate-buffered saline (PBS), pH 7.1. Except during the substrate reaction, plates were incubated at 37° C. for one hour. Plates were washed 10 times between steps with wash buffer (0.02 M sodium phosphate buffer, pH 7.6 with 0.015 M NaCl, 0.05% [V/V] tween-20 and 0.00125% [W/V] thimersol) and were incubated in a humidified box. After coating, wells were blocked with wash buffer containing 1% bovine serum albumin (BSA). Except for the blocking step, in which wells were filled, reagent and sample volumes were 50 µl.

Sample extracts were prepared by grinding tissue in BSA (1:10, W/V). Alkaline phosphatase conjugated BNYVV Ig's was diluted according to the manufacturer's recommendation in BSA. Substrate (p-nitrophenyl phosphate, 4.0 mg/ml in 10% diethanolamine, pH 9.8) was added, and plates were incubated in the dark at 25° C. for 1–18 hours, until the positive controls reacted.

Optical density (OD) values at 410 nm were determined using a Dynatech MR300 ELISA microplate reader (Chantilly, Va.). A sample was considered positive if its OD value was at least three times greater than the mean of the four healthy control samples.

Environmental Data

Environmental data was recorded daily by a CR-21 weather station approximately 2 km from the field test site. Data collected included ambient air temperatures, 10-cm soil temperatures, and precipitation. At the time of each planting, the 10 cm soil temperatures were within 22–27° C. During the first field study, 4 cm of rain fell between planting and final harvest. During the second study, almost 15 cm of rain fell between planting and final harvest.

During both field studies, the 10 cm soil temperatures (approximately 20–28° C.) were within the range for P. betae infection (approximately 15–30° C). With the additive effect of rainfall and irrigation (over 30 cm for each planting) there was also adequate moisture for P. betae to parasitize the growing sugar beet plants. All environmental conditions were seemingly conducive for infection by P. betae and transmission of BNYVV to growing plants.

Results

At the first harvest, approximately one month after the first planting, 46% of the field samples and 50% of the greenhouse samples were positive for BNYWV. At six weeks after planting, the percentage of BNYVV-positive plants had risen to 57% and 80%, respectively. In the second study, the plants were harvested approximately 3.5 months after planting. Both greenhouse and field plants were 90% positive for BNYVV. In all studies, all of the control samples were negative for BNYVV infection.

TABLE 5

| Study | Place | Harvest | Positives[1] |
|---|---|---|---|
| 1 | Field[2] | 1 month | 46 ± 18.5 |
| 1 | Field | 1.5 months | 57 ± 10.5 |
| 2 | Field | 3.5 months | 92 ± 3.3 |
| 1 | Greenhouse[3] | 1 month | 50 |
| 1 | Greenhouse | 1.5 months | 80 |
| 2 | Greenhouse | 3.5 months | 90 |

[1]Assayed by double antibody sandwich ELISA
[2]Values are meant ±2 standard errors of 80 samples (95% confidence interval)
[3]Values represent means of 25 samples Example 2

BNYVV is Not Rapidly Spread in Soil by Irrigation

Field plots were established to test changes in the distribution of BNYVV-infected P. betae over time in fields were soils were artificially infested and to monitor spread of the disease due to irrigation and post harvest soil movement. Rhizomania inoculum, powdered roots of infected plants obtained as described for Example 1, was placed in disease-free plots and movement of the pathogen in irrigation water during the growing season and by tillage after harvest was monitored. The ELISA test described for Example 1 was used to determine whether sugar beet plants distant from the source of the inoculum were infected. Samples were analyzed twice during the growing season, approximately 8 weeks after plant emergence and just prior to harvest.

Contrary to expectations, no plants, other than those in the infested soil, tested positive for BNYVV. Soil samples were analyzed immediately before and after harvest were potted up in the greenhouse to bait out viruliferous P. betae. Again, surprisingly, only soil samples from the inoculated areas were positive for BNYVV.

Example 3

BSBMV Protects Plants From BNYVV Infection

Beta maritima and Beta macrocarpa, which are subspecies of Beta vulgaris (sugar beet) as well as Chenopodium

*quinoa* which is in the same family of plants, are all known to be susceptible to disease caused by BNYVV. BSBMV was tested for its ability to confer in these plants tolerance to BNYVV.

Plants were mechanically inoculated with BNYVV, BSBMV or both viruses. The mechanical inoculation method is well known to those of skill in the art. Leaf tissue of an infected plant was ground in buffer and the extract applied with a glass rod to a leaf of a plant to be inoculated. The host plant leaf had been dusted with the abrasive, carborundum. The glass rod and inoculum was rubbed on the leaf, causing uptake of the applied extract inoculum.

Specifically, local lesions of BSBMV or BNYVV on *C. quinoa* were macerated in 0.1 M potassium phosphate buffer, pH 7.5, with 0.02 M $Na_2SO_3$ and this extract was used to inoculate *C. quinoa*, *B. macrocarpa*, and *B. maritima*. Plants were inoculated with each virus independently or with mixed inoculum. The expression of symptoms of test and control plants was recorded after approximately two weeks, and ELISA tests performed as described for Example 1 were conducted to verify the presence of the viruses in the host plants.

All hosts inoculated with BNYVV alone developed bright yellow local lesions which eventually went systemic in *B. macrocarpa* and *B. maritima*, after which time these plants expired.

*Chenopodium quinoa* inoculated with BSBMV alone developed diffuse, pale yellow local lesions. *B. macrocarpa* and *B. maritima* inoculated with BSBMV alone developed necrotic spots surrounded by purple halos. The BSBMV virus eventually went systemic in *B. maritima* but not in *B. macrocarpa*.

Simultaneous inoculation of both viruses in *C. quinoa* caused a mottled appearance very different from symptoms developed with either virus alone. In *B. macrocarpa* and *B. maritima*, the BSBMV symptom phenotype dominated over the BNYVV phenotype in co-inoculated plants. Mixed infections did not change the systemic reactions of either virus. In mixed infections, none of the plants expressed severe disease symptoms shown in plants infected with BNYVV alone. Thus, infection of plants with BSBMV interfered with expression of severe disease symptoms caused by BNYVV.

Those plants which were inoculated with both BNYVV and BSBMV developed local lesion symptoms of BSBMV only. This indicates that BSBMV interferes with the normal infection process and expression of BNYVV in host plants.

Example 4

Transmission of BSBMV by *P. betae*

Host plants, *Beta maritima*, were mechanically inoculated with BSBMV-FS by the method described for Example 3. After two weeks, roots of the infected plants were inoculated with *P. betae*. Dried root inoculum containing *P. betae* was prepared by obtaining roots from plants infected with *P. betae*. The roots were washed, allowed to dry, pulverized, and separated from soil and other foreign materials by a series of fine-meshed sieves. The resulting inoculum consisted of powdered roots infected with cystosori of *P. betae*. Host plants were inoculated with the fungus by placing the dried root composition (approximately 0.5 g) in the soil near the roots of the plant. Approximately 10–12 weeks after fungus inoculation, the root tissue was harvested and washed. Dried root tissue was ground to a powder and coated onto sugar beet seed with 2% methyl cellulose as described for Example 1.

Seeds were planted in containers and grown in the greenhouse as described for Example 1. Approximately eight weeks after planting, the root tissue of growing plants are harvested and tested for BSBMV infection by indirect DAS-ELISA as described for Example 5, and visually inspected for cystosori of *P. betae*. Roots were positive for both BSBMV and *P. betae*. These results indicate that BSBMV is transmitted to a host plant via soilborne fungus.

Example 5

Characterization of BSBMV

BSBMV was compared with BNYVV using PCR to amplify specified regions of each virus, and comparing restriction enzyme digests of each amplified nucleic acid sequence with that of published sequence data from European isolates of BNYVV (9).

Preparation of BSBMV

BSBMV was propagated in Chenopodium quinoa Willd. by mechanical inoculation with extract from naturally-infected sugar beet leaf tissue ground in 0.1 M potassium phosphate buffer (KPB), pH 7.4, with 0.02 M sodium sulfite. BSBMV was purified from symptomatic *C. quinoa* as described (Kendall et al., 1988, *J. Gen. Virol.*, 69:2335–2345 and 97) with several modifications. 2-mercaptoethanol was added to the grinding buffer to a final concentration of 0.1% (v/v). After the first low-speed centrifugation, the supernatant was strained through Miracloth (Calbiochem, La Jolla, Calif.). After the first high-speed centrifugation, the pellet was resuspended overnight at 4° C. in 0.05 M borate buffer, pH 8.0, 1 mM $Na_2$ EDTA (resuspension buffer). The final pellet was resuspended and used immediately for nucleic acid extraction or stored at −20° C. BNYVV from infected *C. quinoa* and healthy *C. quinoa* extracts used as controls were prepared in the same manner.

Extraction and Chromatography of Viral RNA

Viral RNA was extracted with chloroform and phenol in 2× STE by the method described (87), with 1% sodium dodecyl sulfate (SDS) and precipitated in three volumes of ethanol at −20° C. and electrophoresed in a 1% agarose formaldehyde denaturing gel in the presence of 0.5 μg/ml of ethidium bromide. Nucleic acid sizes were estimated relative to a 0.24–9.5 kb RNA ladder (Gibco BRL, Gaithersburg, Md.). BNYVV or maize chlorotic mottle virus RNA (4.4 kb) were included as controls.

Nucleic acid extracted from two BSBMV isolates BSBMV-NC and BSBMV-FS separated into four discrete bands with estimated sizes of 6.6, 4.4, and 1.0 kb and 6.7, 4.9, 3.4 and 1.8 kb, respectively. The two larger BSBMV RNAs corresponded roughly in size to those of BNYVV RNAs 1 and 2. The 1.8 kb RNA of BSBMV-FS was approximately the same size as BNYVV RNA 3. The BSBMV 3.4 kb RNA did not correspond in size to any RNA reported for BNYVV but was seen in RNA extracted from the BNYVV control. A faint band at the same location was seen in the virus-free *C. quinoa* preparations. In hybridization studies, cDNA probes from non-fractionated BSBMV and BNYVV RNA preparations did not hybridize with the 3.4 kb band.

A BSBMV isolate originally obtained from infected root tissue and purified from *C. quinoa* yielded five RNAs with estimated lengths of 6.7, 4.6, 3.4, 1.8 and 1.4 kb. With the exception of the 3.4 kb band, the RNAs from the root preparation were approximately the size of BNYWV RNAs 1, 2, 3, and 4. The two larger BSBMV RNAs have been detected consistently in different isolates.

Poly A-Analysis

Determination of polyadenylation in the nucleic acid was determined by passing BSBMV-NC nucleic acid (now prepared) through an oligo (dT) cellulose column (Gibco, BRL) according to the manufacturer's instructions. Red clover necrotic mosaic virus and potato virus Y (obtained from Steve Lommel, N.C. State university) were used as non-polyadenylated and polyadenylated controls, respectively. Alternatively, magnetic beads coated with oligo (dT) primers (Promega) were mixed with crude BSBMV-infected *C. quinoa* plant extracts, again following manufacturer's instructions. BNYVV was used as a polyadenylated control. Banding patterns of nucleic acid bound by oligo (dT) in both cases were similar to those produced by BSBMV-NC in the denaturing gel. There was no evidence of a 3.4 kb band.

Viral Protein Analysis

Purified virus was denatured and the virion protein was separated in a discontinuous 12% SDS-polyacrylamide gel (8×7 cm, Hoefer, San Francisco, Calif.). Capsid molecular weight was estimated to be 22.5 K using a 14.3–200 K molecular weight standard (Gibco BRL). BSBMV capsid protein consistently migrated slightly slower than that of BNYWV.

BSBMV and BNYVV coat proteins separated by SDS-PAGE were transferred to nitrocellulose by electrophoresis. The nitrocellulose was probed with BSBMV IgG (ca. 1 μg, antiserum provided by J. E. Duffus, & H. Y. Liu, USDA-ARS, Salinas, Calif.) or BNYVV IgG (1:500, v/v; Biorega-Ag, Chapel Hill, N.C.) and reacted with goat anti-rabbit alkaline phosphatase. Blots were visualized with nitro blue tetrazolium and 5-bromo-4-chloro-3-indolyl phosphate. Proteins reacted with homologous antiserum. No reaction with heterologous antiserum or with healthy *C. quinoa* was detected.

Electron Microscopy

To concentrate virus particles for electron microscopy, extracts from infected sugar beet leaf tissue were processed through the first high-speed centrifugation of the purification procedure. Carbon-coated grids were incubated one hour at 25° C. on the extract, washed with one drop resuspension buffer and two drops distilled water. Particles were stained with two percent phosphotungstic acid, pH 6.2. Particle width was estimated at 19 nm. Particle lengths were divided into 10 nm intervals. The partial purification likely caused virus particles to fracture, resulting in a wide distribution of particle lengths. Modal lengths occurred at 90, 100, 190 and 250 nm. Lengths are approximately those reported for the three shorter BNYVV particles (Putz, 1977 J. Gen. Virol., 35:397–401), with the exception of the 190 nm peak.

Plant Susceptibility to BSBMV

Purified BSBMV-NC was mechanically inoculated to *C. quinoa* and maintained by successive transfers. Symptomatic leaf tissue was ground in KPB with 0.02 M sodium sulfite and mechanically inoculated to leaf tissue of plants to be tested for susceptibility to BSBMV. Host range test plants mock-inoculated with KPB with sodium sulfite were used as controls. Plants were observed periodically for symptom development at least four weeks. At that time, or at the time symptoms were observed, leaf tissue was back-inoculated to *C. quinoa* to verify symptoms were due to BSBMV infection. If symptoms that developed on back-inoculated *C. quinoa* were questionable, the *C. quinoa* leaves were tested by DAS-ELISA for the presence of BSBMV.

Thirty-one plant species in 12 families were assayed for susceptibility to BSBMV. The following plants were tested:

| |
|---|
| <u>Aizoaceae</u> |
| *Tetragonia tetragoniodes* (Pall.) Kuntze |
| <u>Amaranthaceae</u> |
| *Amaranthus hybridus* L. |
| <u>Asteraceae</u> |
| *Cichorium endiva* L. |
| *Helianthus annus* L. |
| *Lactuca sutiva* L. |
| <u>Brassicacea</u> |
| *Brassica oleracea* L. var. *botrytis* L. |
| *B. oleracea* L. var. *capitata* L. |
| *B. oleracea* L. var. *gongylodes* L. |
| *B. rapa* L. |
| *Raphanus sativus* L. |
| <u>Chenopodiaceae</u> |
| *Beta macrocarpa* Guss., |
| *B. maritima* L. |
| *B. vulgaris* L. |
| *Chenopodium album* L. |
| *C. quinoa* Willd. |
| *Spinacia oleracea* L. |
| <u>Cucurbitaceae</u> |
| *Cirtrulls lanatus* (Thunb.) matsum. and Nakai |
| *Cucurbita pepo* L. |
| <u>Fabaceae</u> |
| *Arachis hypogaea* L. |
| *Glycine mar* (L.) Merr. |
| *Phaseolus vulgaris* L. |
| *Vigna unguiculata* (L.) Walp. |
| <u>Malvaceae</u> |
| *Gossypium hirsutum* L. |
| <u>Poaceae</u> |
| *Sorghum bicolor* (L.) Moench |
| *Triticum aestivum* L. |
| *Zea mays* L. |
| <u>Solanaceae</u> |
| *Capsicum annum* L. |
| *Lycopersicon esculentum* Miller |
| *Nictiana tabacum* L. (Samsun and Hicks) |
| *Solanum melongena* L. |
| <u>Tropaeolaceae</u> |
| *Tropaeolum majus* L. |

Those plants known to be susceptible to BNYVV were found to be susceptible to BSBMV. Those plants found not to be susceptible to BSBMV are not known to be susceptible to BNYVV. Host plants and symptoms observed were:

Plants/Symptoms

*Beta vulgaris* L. sparse, pale yellow local lesions, occasional pinpoint necrotic local lesions in ringspot patterns;

*Chenopodium quinoa* Willd. diffuse, pale yellow local lesions that sometimes expanded along leaf veins of inoculated leaves, and bright yellow local lesions have been observed in *C. quinoa* inoculated with other BSBMV isolates;

*Chenopodium album* L.—pale yellow local lesions;

*Spinacia oleracea* L.—subtle systemic mottling;

*Beta maritima* L.—necrotic lesions with yellow halos, followed by development of systemic mottling and stunting of new growth;

*Beta macrocarpa* Guss.—tan or purple necrotic local lesions, chlorotic halos around the necrotic lesions in early stages of infection, and some BSBMV isolates became systemic in inoculated plants;

*Tetragonia tetragoniodes* (Pall.) Kuntze—pale yellow local lesions which later became bright yellow and coalesced, and necrosis of the entire leaf often followed.

Results indicate that BSBMV is a multiparticulate rod-shaped virus made up of, depending on the isolate, 2–4 polyadenylated RNAs. The two larger RNAs have been present in all isolates studied. Variation in the number of smaller RNAs may be due to source of host plant tissue used for virus increase (i.e. leaf vs. root tissue), temperature, time of year the isolate was collected or naturally-occurring variation within the population.

BNYVV, as a proposed member of the furovirus group, differs fundamentally from other furoviruses in that it possesses 3' polyadenylated RNA and is composed of more than two particles. The only other multiparticulate rod-shaped virus transmitted by *P. betae* known to infect sugar beet is beet soil-borne virus (BSBV). It consists of two non-polyadenylated RNA species of approximately 3.6 and 3.2 kb, with a possible 6.0 kb RNA (Kaufman, et al., 1992, *Intervirology,* 33:97–102). Because of the size of the RNAs and lack of a poly (A) tail, it is considered more similar to other members of the furovirus group than to BNYVV. No serological cross-selection was detected between BSBMV and BNYVV using polyclonal antibodies in this study. BSBMV is serologically different from BNYVV and causes foliar symptoms in systemically infected sugar beets that are distinct from those caused by BNYVV. Based on particle number and morphology, transmission by *P. betae* and the presence of polyadenylated RNA, it is suggested that BSBMV be considered a member of the furovirus group, more similar to BNYVV than to other furoviruses.

Virus Maintenance

BNYVV and BSBMV isolates were obtained from infected sugar beets from Texas, California, and Nebraska (Table 1). Initial isolate selection was based on serology (ELISA) and diagnostic root and foliar symptoms for BNYVV and BSBMV, respectively. Isolates were maintained in the greenhouse in *Chenopodium quinoa* Willd. by repeated mechanical inoculation or in sugar beet root cultures.

Polymerase Chain Reaction

A primer pair was synthesized for BNYVV RNA 1 based on published nucleotide sequence data from European isolates (9). The downstream primer BNYVV 1 SEQ ID 1=(5' TTC ACA AGT CAG TA 3') is complementary to bases 6688 to 6704 of RNA 1 but the sequence is common to all four RNA species of BNYVV. The upstream primer BNYVV 3 SEQ ID 2=(5' AGA TAG TGC TAT AAA CGG 3') is identical to bases 5649 to 5666 and is specific for RNA 1.

Crude nucleic acid extracts of purified BNYVV and BSBMV RNA were used as templates for first strand cDNA synthesis in reverse transcriptase reactions. Extracts from noninfected plants were used as controls. Two microliters of sample were mixed with 0.2 M 2-mercaptoethanol, 10 pmol BNYVV 1, 10 mM dNTP's, 3.5 U AMV reverse transcriptase (Boehringer Mannheim), 5 µl 5× reaction buffer, supplied with the enzyme, and H$_2$O to a final volume of 20 µl. The solution was incubated at 40° C. for one hour, diluted to 40 µl with H$_2$O and boiled five minutes to stop the reaction.

PCR amplification was carried out in 50 µl reactions using 2 µl cDNA, 10 pmol of each primer, 10 mM dNTP's, 2.5 U Taq DNA polymerase (Perkin-Elmer), 5 µl of 10× reaction buffer supplied with the enzyme, and H$_2$O to volume. The mixture was overlaid with 100 µl mineral oil and subjected to 35 cycles consisting of one minute at 94° C., one minute at 41° C., and two minutes at 72° C. During the first and last cycle, the extension step was held at 72° C. for 10 minutes, and the reaction mixture was held at 4° C. after the final cycle. PCT products were analyzed by electrophoresis in one percent agarose gels followed by staining with ethidium bromide. In some experiments, BNYVV and BSBMV RNA were mixed and used in the cDNA reaction. Alternatively, cDNA made from the different extracts were mixed and used in PCR.

To verify the identity of amplified products, bands of the expected size were cut from gels and DNA was extracted using the Gene Clean Kit (Biosis 101). Purified DNA was digested with restriction enzymes Dra I, Tha I, Nhe I, and Spe I following manufacturer's instructions. Based on the published nucleotide sequence of BNYVV, each of these enzymes was expected to digest the BNYVV PCR product at only one site, with the exception of Dra I with three predicted restriction sites. Digestion products were analyzed by electrophoresis in one percent agarose gels after staining with ethidium bromide.

Results

A PCR product of the expected size was produced by PCR amplification by BNYVV cDNA using two primers BNYVV 1 and BNYVV 3. The same product was obtained using either crude nucleic acid extracts or purified virion RNA preparations. Somewhat unexpectedly, a PCR product was also produced when the BNYVV primers and BSBMV cDNA template were used. This product, approximately 1000 bp compared to 1056 bp for the BNYVV product was produced with all BSBMV isolates tested. However, when BNYVV was mixed with BSBMV, either as RNA samples for first strand cDNA synthesis or as cDNA in PCR, only the BNYVV product was amplified.

When exposed to restriction enzyme digestion, both BNYVV and BSBMV PCR products were digested by Dra I, Nhe I, and Spe I, as predicted from BNYVV nucleotide sequence data. However, Tha I only digested the BSBMV product. When BSBMV cDNA was mixed with BNYVV cDNA and amplified by PCR, the single resulting product was not digested by Tha I, further indicating that only BNYVV cDNA was amplified in mixed samples. In all cases, restriction fragments corresponding to the 5' ends of BNYVV and BSBMV were similar in size, while those corresponding to the 3' end of the fragments of BSBMV were smaller than those of BNYVV. These results suggested that the nucleotide sequence of the BSBMV product is quite similar to that of the BNYVV product and that the size difference between the two products is likely due to a small deletion near the 3' end of BSBMV RNA 1.

After determining that primers BNYVV 1 and BNYVV 3 directed amplification of a cDNA product unique for BSBMV, the BSBMV PCR product was cloned to Hinc II digested pGEM3z and partially sequenced from each end by the dideoxy method of Sanger et al. Based on the preliminary nucleotide sequence data, two primers specific for BSBMV were synthesized. The upstream primer BSBMV-1 SEQ ID 3 (5' TAC GCA ACT CAT TGA AAG GTA 3') is identical to bases 66–86 of the BSBMV PCR product and the downstream primer BSBMV-2 SEQ ID 4 (5' AGA TAA CAC TTG TAA CTC GTC 3') is complementary to bases 737 to 756. Using these primers and BSBMV cDNA from several isolates, the expected PCR product of 691 bp was obtained. The primers BSBMV-1 and -2 did not allow the amplification of BNYVV cDNA, and when BNYVV and BSBMV cDNA were mixed and used in PCR, only the 691 bp product of BSBMV was amplified. This product was digested with Tha I, verifying its origin from BSBMV.

The results of this study support conclusions that BSBMV is very closely related to BNYVV. Primers specifically designed for BNYVV RNA 1 matched BSBMV RNA well enough to allow amplification of a PCR product. However, in the presence of both viruses, the precise match of BNYVV primers with BNYVV templates likely allowed more efficient DNA amplification than with BSBMV templates. Thus, the homologous BNYVV PCR products predominated in PCR reactions with mixtures of BNYVV and BSBMV cDNAs. Furthermore, the BSBMV product had Dra I, Nhe I, and Spe I restriction sites in common with the BNYVV PCR product. The BSBMV product was also digested by Tha I, but not the BNYVV product, as predicted. This indicates the nucleotide sequence of the BNYVV isolate used in this study differs from the published sequence of the European isolate in at least one restriction site near the 3' end of RNA 1.

Although genetic variation is likely among isolates of BSBMV, RT-PCR products from different isolates appeared identical. Whether products were amplified using the BNYVV primer pair or BSBMV-1 and -2, the PCR products produced with a given primer pair were apparently identical in size and restriction digestion profile. More importantly, BNYVV and BSBMV were easily detected and differentiated in infected plant tissue. If cDNA made from BSBMV or BNYVV extracts were mixed, the two primer pairs only directed the amplification of the homologous cDNA. Thus, if a plant is infected with both viruses, only one will be detected with a given set of primers. However, if the 1000 bp BSBMV product is amplified using the BNYVV primer pair, no BNYVV is present in the sample. This can be verified by restriction analysis with Tha I.

Example 6

Effect of Established BSBMV-Infected *P. betae* on the Spread of BNYVV-Infected *P. betae*

Sugar beet plants are grown in small microplots and infected with BSBMV either directly as described for Example 3 or via viruliferous *P. betae* as described for Example 4. The infected beet plants are grown for several weeks to allow a population of *P. betae* infected with BSBMV to become established in the soil. Plant infection by BSBMV is verified by ELISA, after which the plants are removed and the soil in each microplot is mixed to simulate harvest and plowing. Fresh, uninfected beet plants or seeds are planted in the presence or absence of BNYVV inoculum in the soil. Plots without an established BSBMV-infected fungus population are planted as a control. Approximately 8–10 weeks after infesting plots with BNYVV and planting, plants are inspected for phenotypic expression of virus and beets are harvested and evaluated by ELISA for infection by BSBMV and BNYVV.

Example 7

Sugar Beet Plants Tolerant to BNYVV

Sugar beet seeds are coated with viruliferous fungus carrying BSBMV by the seed coating method described for Example 1. Seeds are planted in soil and grow into plants infected with BSBMV, as determined by ELISA or by expression of mild disease symptoms. Subsequent challenge with BNYVV either by mechanical inoculation or by soilborne fungus infection results in sugar beet plants which fail to express severe symptoms of Rhizomania.

Example 8

One Example of Transmission of a Foreign Nucleic Acid Sequence to a Host Plant

In one example of transmission of a foreign nucleic acid sequence, a foreign gene is vectored into a host plant susceptible to a soilborne fungus via a viruliferous virus via the viruliferous fungus coated seed method of the present invention. For example, a foreign nucleic acid sequence, e.g., the DNA sequence encoding the commercially available marker GUS is first incorporated into a virus such as the furovirus serotype BSBMV This may be accomplished by methods known to those of skill in the art, e.g., by restriction enzyme digestion and ligation methods (87).

The furovirus is then used to inoculate a host plant, which plant is grown in soil containing a soilborne fungus, such as Polymyxa. The virus infects the fungus, and the fungus-infected plant roots or cystosori are harvested. The powdered viruliferous fungus infected plant roots or cystosori are mixed with an aqueous solution of a polymer such as methyl cellulose, and coated onto seed of a host plant. When planted into soil and permitted to grow, the viruliferous infects the growing plant, thereby vectoring the foreign nucleic acid sequence in the plant. The plant tissue is harvested and assayed for the expression of the inserted nucleic acid sequence by known methods, e.g., by ELISA or visual inspection for phenotypic expression. Specific details of this type of experiment are described below.

Clone Construction

Full-length, infectious cDNA clones are constructed using standard recombination and molecular biological techniques. As detailed above, six overlapping clones which, in sum, cover the full length of BSBMV RNA 2 (except the 5' terminus) have been cloned. The existence of restriction sites within the areas of overlap between succeeding clones enables us to piece together these sequences into a full-length cDNA or RNA 2, which can be grown as a clone using standard *E. coli* transformation (88). Methods developed for generation of cDNA clones in BNYVV (75,114) are be used to obtain cDNA clones of BSBMV. The development of full-length cDNA clones of the other RNA species or other furoviruses including, but not limited to SBWMV, PCV, OGSV, PMTV, RSNV, and SCSV, can use the same type of cut-and-paste approach. Gene substitutions or additions can initially focus on RNA 2 cDNA and native RNA's 1, 3, 4 and 5. After the completion of sequencing of BSBMV RNA 3 development of RNA 3 cDNA clones can then be accomplished. Owing to the size of RNA 3 (about 1700 nt), it is possible to directly obtain a full-length clone using oligo-dT-primed PCR.

Because the presence of RNAs 1 and 2 and the 5' and 3' cis-regulatory domains of RNA 3 are sufficient to drive the amplification and expression of a foreign gene in infected tissue, full-length cDNA clones of RNA 3 may not be necessary. Construction of cDNA clones encoding RNAs 1, 2 and the 5' and 3' cis-regulatory domains of RNA 3 along with the foreign gene of interest may, in some cases, be sufficient.

In Vitro Transcription

To generate infectious artificial RNA transcripts from cDNA clones, the methods outlined previously by BNYVV (75,114) can be utilized.

Briefly, recombinant plasmids can be obtained in which plus-strand RNA synthesis is under the control of a T7 promotor and T7 polymerase-mediated transcription can be conducted in the presence of RNAsin, and $m^7GpppG$ for production of capped transcripts. The size and integrity of the transcripts is determined via formaldehyde-agarose gel electrophoresis, followed by transfer to nitrocellulose and standard RNA-blot hybridization using $^{32}$P-labeled antisense probes (88).

Biological Assay

In order to evaluate transcript activity, freshly prepared RNA 2 and RNA 3 transcript are added to a mixture of BSBMV RNA 1, 3, and 4 or 1, 2 and 4 respectively. The BSBMV RNA can be phenol-extracted from local lesions on *Chenopodium quinoa* (49). Individual RNA species of BSBMV can be separated in low-melting-point agarose gels by electrophoresis, purified using silica particles (RNaid, Bios 101), and then mixed with the transcripts. Leaves of *C. quinoa* can be dusted with carborundum and mechanically inoculated with the transcript-viral RNA mixture.

Controls include mock-inoculated plants and plants inoculated with viral RNA without the transcript. Because the transcript RNA is infectious, local lesions will appear on inoculated leaves of the plants in a few days. For *C. quinoa*, lesions will appear in 6–9 days. RNA can then be extracted from symptomatic leaves, separated in agarose gels, and analyzed by RNA-blot hybridization (81,88,114) using cDNA probes specific to each of the BSBMV RNAs. When artificial RNA 2 transcript is used in the initial inoculation mixture, total soluble plant proteins from symptomatic leaves can also be tested for the presence of BSBMV coat protein immunologically, after SDS-PAGE and transfer to nitrocellulose membranes (48,88).

Marker Gene Constructs

Any known plant marker gene can be used in combination with any promoter known to be functional in plants. For example, GUS or Bar genes can be used as markers, in combination with the CaMV 35S or Ti NOS promoter regions and the NOS 3' untranslated region. These constructs can be inserted into several sites of BSBMV RNA 2, using standard recombinant-DNA methods (88). One site that can be used for insertion of the constructs is a region which is deleted in BSBMV compared to the BNYVV sequence, a region about 500 nt long, beginning immediately after the termination site of ORF-1 (at nt 724 of the BNYVV RNA 2 sequence). This apparent deletion occurs in a region in which readthrough occurs in both viruses, generating ORF-2. ORF-2 terminates at nt 2220 of BNYVV and at nt 1863 of BSBMV. If the total insertion is too long to be properly packaged, an in-frame insertion of the marker gene alone, using viral untranslated regions, can be effective in this region. ORF-3 in BSBMV RNA 2 is 1072 bp long, so gene substitution can also be done here. If the product of ORF-3 is essential, complementation can be practiced by using the guard-cell line developed by Hall et al. (40) to introduce the intact ORF-3 into sugar beets. The work of Jupin, et al. (54) suggests that much of RNA 3 may be expendable and therefore a useful site for gene replacement.

Gene Expression (Data Analysis)

Evaluations are performed over time after initial inoculation, as well as in extracts of various plant organs. Spatial variation in expression may be evaluated through tissue printing (88). GUS enzymatic activity is identified by a modification of Jefferson's (53) technique, and quantified by using methyl-umbelliferyl-β-D-glucuronide (MUG) as substrate. Bar-encoded activity of phosphinothricin acetyl transferase (PAT) is assayed using a modification of the procedure of DeBlock, et al. (22), and a prescreening method (112). Expression can be evaluated in above-ground organs as well as roots.

Other marker genes can be assayed for expression and quantified by their known techniques. These include, but are not limited to, the gene encoding β-galactosidase activity, chloramphenicol acetyl transferase, luciferase, and green-fluorescent protein. β-galactosidase activity can be assessed by feeding the transgenic plants X-gal. Plant cells containing both X-gal and expressing β-galactosidase will turn blue, the intensity of which is directly proportional to the amount of β-galactosidase gene expression.

Gene Expression Through the Fungal Vector

In order to achieve expression of a foreign gene in seedlings arising from seed treated with viruliferous *P. betae* cystosori, the following experiments are performed. *Beta vulgaris* var. *maritima*, a systemic host to BSBMV, is mechanically inoculated with full-length, infectious transcripts and complimentary viral RNAs from BSBMV as described above. Wild type BSBMV and mock-inoculated plants are included as controls. Approximately two weeks after systemic infection is first observed, plants are inoculated with aviruliferous *P. betae* (either zoospores or dried roots containing cystosori can be used) (36). Leaf and root samples will be taken at this time to test for expression of the foreign gene. Plant expressing the foreign gene can then be grown for an additional 8 to 10 weeks to allow time for thorough root colonization, virus uptake and formation of cystosori by *P. betae*. Resultant cystosori will be viruliferous and will contain the recombinant virus. After it has been verified microscopically that cystosori have formed, plants can be harvested and roots dried. Dried roots containing viruliferous cystosori can be used to coat seed of *B. vulgaris* vars. *vulgaris* and *maritima* as previously described (41). Resulting seedlings can be harvested sequentially over a four week period and tested for expression of the foreign gene as described above. Cystosori from these plants can be collected and used to repeat the experiment in a second cycle. This can be continued for at least five cycles or until the foreign gene can no longer be detected. Thus, these experiments illustrate foreign gene transfer to and expression in plant cells via the seed coating method.

Example 9

Survival of Foreign Gene in Cystosori

The limited host ranges of both virus and fungal vector limit the environmental danger that survival of a foreign gene in cystosori would pose. In addition, although cystosori survive in the soil for several years, populations decline over time and the fungal vector doesn't move rapidly through infested soil (43,105). However, testing for gene survival through several cycles of plant infection and cystosori formation can directly determine how long a specific foreign gene will survive within the cystosori, and how various conditions will affect its expression.

To determine survival of foreign gene expression, *Beta vulgaris* var. *maritima*, a systemic host to BSBMV, can be mechanically inoculated with full-length, infectious transcripts and complimentary viral RNAs from BSBMV containing a reporter gene linked to a promoter. Wild type BSBMV and mock-inoculated plants can be included as controls. Approximately two weeks after systemic infection is first observed, plants can be inoculated with aviruliferous *P. betae* (either zoospores or dried roots containing cystosori can be used) (36). Leaf and root samples can be taken at this time to test for expression of the foreign (marker) gene. Plant expressing the foreign gene can then be grown for an additional 8 to 10 weeks to allow time for thorough root colonization, virus uptake, and formation of cystosori by *P. betae*. Resultant cystosori will be viruliferous and contain the recombinant virus.

Conditions that mimic environmental conditions faced by cystosori can be simulated to test for alterations of foreign gene expression caused by such conditions. For example, dried roots containing cystosori from several plants treated as above can be subjected to different conditions, including but not limited to variations in temperature (−50° C. to 50° C.), mechanical stress, soil-water content (0–100% $H_2O$ content), and soil-nutrient content, for varying lengths of time (1–4 weeks, for example). Dried roots containing viruliferous cystosori can be used to coat seed of *B. vulgaris* vars. *vulgaris* and *mantima* as previously described (41). Resulting seedlings can be harvested sequentially over a four week period after being subjected to said conditions, and then tested for alterations of expression of the foreign gene as described above. Expression of the foreign gene can be evaluated both in above-ground organs as well as in roots.

To address additional concerns about environmental hazards, additional experiments can be conducted in which aviruliferous *P. betae* cystosori and *P. betae* cystosori with wild type BSBMV are mixed with cystosori containing the recombinant virus. These mixtures can be used to coat seed of *B. vulgaris* vars. *vulgaris* and *maritima* as previously described (41). Resulting seedlings can be harvested over a four week period and tested for the presence or absence of wild type or recombinant sequences. A greater number of the resulting seedlings will contain the wild type BSBMV because recombinant viruses do not compete well with wild type viruses.

Example 10

The Use of the Seed Coating Delivery System to Deliver an Agronomically Desirable Trait The seed coating delivery system can be used to deliver the gene encoding $H_2O_2$-generating glucose oxidase to plants. Plants expressing glucose oxidase exhibit strong resistance to a bacterial soft rot disease caused by *Erwinia carotovora* subsp. *carotovora* (111). Production of active oxygen species is a defense response to pathogen infection of many plants. Plants expressing a fungal gene encoding glucose oxidase, which generates $H_2O_2$ when glucose is oxidized can be obtained by using the seed coating delivery system of the present invention in order to confer disease-resistance properties to various plants. Specifically, the gene encoding glucose oxidase can be cloned into the correct position within the RNA2 species of BSBMV as determined through the experiments described in the "Marker Gene Construct" section above.

In order to achieve expression of glucose oxidase in seedlings arising from seed treated with viruliferous *P. betas* cystosori, *Beta vulgaris* var. *maritima*, a systemic host to BSBMV, can be mechanically inoculated with full-length, infectious transcripts and complimentary viral RNAs from BSBMV containing the glucose oxidase gene. Wild type BSBMV and mock-inoculated plants can be included as controls. Approximately two weeks after systemic infection is first observed, plants can be inoculated with aviruliferous *P. betae* (either zoospores or dried roots containing cystosori can be used) as described above. Leaf and root samples can be taken at this time to test for expression of the glucose oxidase which can be determined by measuring $H_2O_2$ levels in both leaf and tuber tissues.

Plants expressing high levels of glucose oxidase can then be grown for an additional 8 to 10 weeks to allow time for thorough root colonization, virus uptake, and formation of cystosori by *P. betae*. Resultant cystosori will be viruliferous and will contain the recombinant virus., After it has been verified microscopically that cystosori have formed, plants can be harvested and roots dried. Dried roots containing viruliferous cystosori can be used to coat seed of *B. vulgaris* vars. *vulgaris* and *maritima* as previously described (41).

Alternatively, other viral vector/fungal systems can be used to transfer the $H_2O_2$-generating glucose oxidase. The $H_2O_2$-generating glucose oxidase has been tested in potato plants (e.g. *Solanum tuberosum* L.) (111). Thus, an alternative to the *P. betae*/BSBMV fungaviral vector system is the potato mop top virus (PMTV) and the vector fungus *Spongospora subterranea*. Potato plants can be mechanically inoculated with full-length, infectious transcripts and complimentary viral RNAs from PMTV containing the glucose oxidase gene as described above for BSBMV. Wild type PMTV inoculated and mock-inoculated *Spongospora subterranea* can be included as controls. Approximately two weeks after systemic infection of *Solanum tuberosum* L. is first observed, leaf and root samples can be taken to test for expression of the glucose oxidase which can be determined by measuring $H_2O_2$ levels in both leaf and tuber tissues.

Potato plants expressing high levels of glucose oxidase can then be grown for an additional 8 to 10 weeks to allow time for thorough root colonization, virus uptake, and formation of cystosori by *Spongospora subterranea*. Resultant cystosori will be viruliferous and will contain the recombinant virus., After it has been verified microscopically that cystosori have formed, plants can be harvested and roots dried. Dried roots containing viruliferous cystosori can be used to coat seed of *Solanum tuberosum* L as previously described for the sugar beet(41).

Example 11

Transfer of a Recombinant Virus Using the Seed Coating Technique

While the above examples illustrate the use of this invention for the transfer of a desired foreign gene of interest to a plant cell, due to the very nature of the invention, these examples also illustrate the transfer of a recombinant virus to plant cells. In each of these examples, it was not the virus per se that was of interest to the transfer, but rather the gene that the virus carried. However, in principle, any virus that is desired to be transferred can be used via the same invention technique.

The foregoing disclosure and description of the invention are illustrative and explanatory thereof, and various changes in the details of the illustrated apparatus and construction and method of operation may be made without departing from the spirit of the invention.

References

1. Abe, H., and T. Tamada, 1986. Association of beet necrotic yellow vein virus with isolates of *Polymyxa betas* Keskin. Ann Phytopath. Soc. Japan 52:235–247.
2. Abe, H., and T. Ui. 1986. Host range of *Polymyxa betae* Keskin strains in rhizomania-infested soils of sugar beet fields in Japan. Ann. Phytopath. Soc. Japan 52:394–403.
3. Ahlquist, P., R. French, M. Janda, L. S. Loesch-Fries. 1984. Multicomponent RNA plant virus infection derived from cloned viral cDNA, P.N.A.S. U.S.A. 81:7066–7070.
4. Barr, D. J. S. 1979. Morphology and host range of *Polymyxa graminis, Polymyxa betae*, and *Ligniera pilorum* from Ontario and some other areas. Can. J. Plant Pathol. 1:85–94.
5. Barr, D. J. S. 1988. Zoosporic plant parasites as fungal vectors of viruses: Taxonomy and life cycles of species involved. pp. 123–137 In:

Development in Applied Biology 2, Viruses with Fungal Vectors, J. I. Cooper and M. J. C. Asher, eds. Univ. of St. Andrews, UK.
6. Barr, K. J. and M. J. C. Asher. 1992. The host range of *Polymyxa betae* in Britain. Plant Pathol. 41:64–68.
7. Beachy, R. N., S. Loesch-Fries, and N. E. Tumer. 1990. Coat protein-mediated resistance against virus infection. Annu. Rev. Phytopathol. 28:451–474.
8. Bouzoubaa, S., H. Guilley, G. Jonard, J. Jupin, L. Quillet, K. Richards, D. Scheidecker, and V. Ziegler-Graff. 1988. Genome organization and function of beet necrotic yellow vein virus. Develop. Appl. Biol. 2:99–110.
9. Bouzoubaa, S., L. Quillet, H. Guilley, G. Jonard, and K. Richards. 1987. Nucleotide sequence of beet necrotic yellow vein virus RNA-1. J. Gen. Virol. 68:615–626.
10. Bouzoubaa, S., V. Ziegler, D. Beck, H. Guilley, K. Richards, and G. Jonard. 1986. Nucleotide sequence of beet necrotic yellow vein virus RNA-2. J. Gen. Virol. 67:1689–1700.
11. Bouzoubaa, S., H. Guilley, G. Jonard, K. Richards, and C. Putz. 1985. Nucleotide sequence analysis of RNA-3 and RNA-4 of beet necrotic yellow vein virus, isolates F2 and G1. J. Gen. Virol. 66:1553–1564.
12. Boyer, J. C. and A. L. Haenni. 1994. Infectious transcripts and cDNA clones of RNA viruses. Virology 198:415–426.
13. Brisson N., J. Paszkowski, J. R. Penswick, B. Gronenbom I. Potrykus and T. Hohn. 1984. Expression of a bacterial gene in plants by using a viral vector. Nature 310;511–514.
14. Brunt, A. A., and K. E. Richards. 1989. Biology and molecular biology of furoviruses. Adv. Virus Res. 36:1–32.
15. Brunt, A. A., E. Shikata. Fungus-transmitted and similar labile rod-shaped viruses. In: The Plant Viruses: Volume 2, The Rod-Shaped Plant Viruses. M. H. V. Van Regenmortel and Heinz Fraenkel-Conrat, eds. Plenum Press, NY. pp. 305–335.
16. Chapman, S., T. Kavanagh and D. Baulcombe. 1992. Potato virus X as a vector for gene expression in plants. Plant J. 2:549–557.
17. Christensen A. H. and P. H. Quail. 1996. Ubiquitin promoter-based vectors for high-level expression of selectable and/or screenable marker genes in monocotyledonous plants. Transg. Res. 5:213–218.
18. Christou, P., D. G. McCabe, and W. F. Swain. 1988. Stable transformation of soybean callus by DNA-coated gold particles. Plant Physiol. 87:671–674.
19. D'Halliun, K, E. Bonne, M. Bossut, and M. DeBeuckeleer and H. Leemans. 1992. Transgenic maize plants by tissue electroporation. Plant Cell 4:1495–1505.
20. Datta, S. K., A. Peterhaus, K. Datta and C. Potrykus. 1990. Genetically engineered fertile Indica rice recovered from protoplasts. Bio/Technol. 8:736–740.
21. Dawson, W. O., P. Bubrick and G. L. Grantham. 1988. Modifications of the tobacco mosaic virus coat protein gene affecting replication, movement, and symptomatology. Phytopathol. 78:783–789.
22. De Block, M., J. Botterman, M. Vandiwiele, J. Dockx, C. Thoen, V. Gosselle, N. Rao Movva, C. Thompson, M. Van Montagu, and J. Leemans. 1987. Engineering herbicide resistance in plants by expression of a detoxifying enzyme. EMBO J. 6:2513–2518.
23. De la Pena, A., H. Lorz, and J. Schell. 1987. Transgenic rye plants obtained by injecting DNA into young floral tillers. Nature 325:274–276.
24. Delacioppa G. 1996. Production of biopharmaceuticals in higher plants by transfection with RNA viral vectors. In Vitro 32:22A.
25. Deom, C. M., M. J. Oliver, and R. N. Beachy. 1987. The 30-kilodalton gene product of tobacco mosaic virus potentiates virus movement. Science 237:389–394.
26. Dinant, S., F. Blaise, C. Kusiak, S. Astier-Manifacier, and J. Albouy. 1993. Heterologous resistance to potato virus Y in transgenic tobacco plants expressing the coat protein gene of lettuce mosaic potyvirus. Phytopathol. 83:818–824.
27. Dolja, V. V., H. J. McBride, J. C. Carrington. 1992. Tagging of plant and potyvirus replication and movement by insertion of β-glucuronidase into the viral polyprotein. P.N.A.S. U.S.A. 89:10208–10212.
28. Donson, J., C. M. Kearney, M. E. Hilf, and W. O. Dawson. 1991. Systemic expression of a bacterial gene by a tobacco mosaic virus-based vectors. P.N.A.S. U.S.A. 88:7204–7208.
29. Duffus, J. E., and H. Y. Liu. 1987. First report of rhizomania of sugar beet from Texas. Plant Dis. 71:557.
30. Dunwell, J. M. 1985. Anther and ovary culture In. Cereal Tissue and Cell Culture, S W. J. Bright and M. G. K. Jones, eds., Martinus Nijhoff/W. Junk, Dorbrecht. pp. 1–44.
31. Fauquet, C., D. Desbois, D. Fargette, and G. Vidal. 1988. Classification of furoviruses based upon the amino acid composition of their coat proteins. In.: Development in Applied Biology 2, Viruses with Fungal Vectors, J. I. Cooper and M. J. C. Asher, eds., Univ. of St. Andrews, UK, pp. 19–36.
32. Fraley, R. T., S. G. Rogers, R. B. Horsch, P. R. Sanders, J. S. Flick, S. P. Adams, M. L Bittner, L. A. Brand, C. L. Fink, J. S. Fry, G. R. Galluppi, S. B. Goldberg, N. L. Hoffmann, and S. C. Wood. 1983. Expression of bacterial genes in plant cells. P.N.A.S. U.S.A. 80:4803–4807.
33. Fry, J. E., A. R. Barnason, and M. Hinchee. 1991. Genotype-independent transformation of sugar beet using Agrobacterium tumefaciens. In. Molecular biology and plant development, Proc. Third International Congress of the ISPMB, Tuscon, U.S.A. Abstract No. 384.
34. Fulton, R. W. 1986. Practices and precautions in the use of cross protection for plant virus disease control. Ann. Rve. Phytopathol. 24:67–81.
35. Gera, A, C. M. Deom, J. Donson, J. J. Shaw, D. J. Lewandowski, and W. O. Dawson. 1995. Tobacco mosaic tobamovirus does not require concomitant synthesis of movement protein during vascular transport. Mol. Plant-Microbe Interact. 8:784–787.
36. Gerik, J. S. 1992. Zoosporic obligate parasites of roots. In: Methods for Research on Soilborne Phytopathogenic Fungi. L. L. Singleton, J. D. Mihail, and C. M. Rush (eds.). APS Press, St. Paul, Minn. pp. 18–24.
37. Gerik, J. S., and J. E. Duffus. 1988. Differences in vectoring ability and aggressiveness of isolates of *Polymyxa betae*. Phytopathol. 78:1340–1343.
38. Gerik, J. S., and J. E. Duffus. 1987. Host range of California isolates of *Polymyxa betae*. Phytopathol. 77:1759.
39. Gruber, M. Y. and W. L. Crosby. 1993. Vectors for plant transformation. In. Methods in Plant Molecular Biology and Biotechnology, B. R. Glick, and J. E. Thompson, eds. CRC Press, Boca Raton, pp. 89–119.
40. Hall, R. D., T. Riksen-Bruinsma, G. J. Weyeus, I. J. Rosquin, P. N. Denys, I. J. Evans, J. E. Lathonwers, M. P. Lefebure, J. M. Dunwell, A. V. Tunen, and F. A. Krens. 1996. A high efficiency technique for the generation of transgenic sugar beets from stomatal guard cells. Nature Biotechnol. 14:1133–1138.
41. Harveson, R. M., and C. M. Rush. 1993. A simple method for field and greenhouse inoculation of *Polymyxa*

*betae* and beet necrotic yellow vein virus. Phytopathol. 83:1216–1219.
42. Harveson, R. M., and C. M. Rush. 1993. Movement of viruliferous *Polymyxa betas* from a point source inoculation. J. Sugar Beet Res. 30:97.
43. Harveson, R. M., C. M. Rush, and T. A. Wheeler. 1996. The spread of beet necrotic yellow vein virus from point source inoculations as influenced by irrigation and tillage. Phytopathol. 86:1242–1247.
44. Hayes, R. J., R. H. A. Coutts, and K. W. Buck. 1989. Stability and expression of bacterial genes in replicating geminivirus vectors in plants. Nucleic Acids Res. 17:2391–2403.
45. Heidel, G. B., and C. M. Rush. 1993. Distribution of beet necrotic yellow vein virus beet distortion mosaic virus and an unnamed soilborne sugar beet virus in Texas and New Mexico. Plant Dis. 78:603–606.
46. Heidel, G. B. and C. M. Rush. 1995. Effects on growth of two sugar beet cultivars infected by BNYVV,BSBMV, or BNYVV+BSBMV, American Society of Sugar Beet Technologists Proc., New Orleans, La.
47. Heidel, G. B., C. M. Rush, T. L. Kendall, and S. A. Lommel. 1993. Partial characterization of a soilborne sugar beet virus in Texas. J. Sugar Beet Res. 30:98.
48. Heidel G. B., C. M. Rush, T. L. Kendall, S. A. Lommel, and R. C. French. 1996. Characteristics of beet soilborne mosaic virus, a furo-like virus infecting sugar beet. Phytopathol. (submitted).
49. Hiei, Y., S. Ohta, T. Komari and T. Kumasho. 1994. Efficient transformation of rice (*Oryza sativa* L.) mediated by Agrobacterium and sequence analysis of the boundaries of the T-DNA. Plant J. 6:271–282.
50. Horsch, R. B., J. Fry, N. L. Hoffmann, M. Wallroth, D. Eichholtz, S. G. Rogers, and R. T. Fraley, 1985. A simple and general method for transferring genes into plants. Science 227:1229–1231.
51. Horsch, R. B., R. T. Fraley, S. G. Rogers, H. J. Klee, J. Fry, and M. Hinchee. 1987. Agrobacterium-mediated gene transfer to plants: Problems and Prospects. In. Plant Bio/technology—Research Bottlenecks for Commercialization and Beyond, T. J. Mabry, ed., IC$^2$ Institute, Austin, Tex., pp. 9–26.
52. Ishida Y., H. Saito, S. Ohta, Y. Hiei, T. Komari, and T. Kumashiro. 1996. High efficiency transformation of maize (*Zea mays* L.) mediated by *Agrobacterium tumefaciens*. Nature Biotechnol. 14:745–750.
53. Jefferson, R. A. 1987. Assaying chimeric genes in plants the gene fusion system. Plant Mol. Biol. Rep. 5:387–405.
54. Jupin, I., H. Guilley, K. E. Richards, and G. Jonard. 1992. Two proteins encoded by beet necrotic yellow vein virus RNA 3 influence symptom phenotype on leaves. EMBO J. 11:479–488.
55. Jupin, I., K. Richards, G. Jonard, H. Guilley, and C. W. A. Pleu. 1990. Mapping sequences required for productive replication of beet necrotic yellow vein virus RNA3. Virology 178:273–280.
56. Jupin, I., T. Tamada, and K. Richards. 1991. Pathogenesis of beet necrotic yellow vein virus. Virology 2:121–129.
57. Kaeppler, H. F., D. A. Somers, H. W. Rines, and A. F. Cockburn. 1992. Silicon carbide fiber-mediated stable transformation of plant cells. Theor. Appl. Genet. 84:560–566.
58. Klee, H., R. Horsch, and S. Rogers. 1987. Agrobacterium-mediated plant transformation and its further applications to plant biology. Annu. Rev. Plant Physiol. 38:467–486.
59. Klein, T. M., E. D. Wolf, R. Wu, and J. C. Sanford. 1987. High-velocity microprojectiles for delivering nucleic acid into living cells. Nature 327:70–73.
60. Koenig, R., and W. Burgermeister. 1989. Mechanical inoculation of sugarbeet roots with isolates of beet necrotic yellow vein virus having different RNA compositions. J. Phytopathol. 124:249–255.
61. Koenig, R., W. Burgermeister, H. Weich, W. Sebald, and C. Kothe. 1986. Uniform RNA patterns of beet necrotic yellow vein virus in sugarbeet roots, but not in leaves from several plant species. J. Gen. Virol. 67:2043–2046.
62. Krens, F. A., C. Zijistra, Van der Molen, W., D. Jamar, and H. J. Huizing. 1988. Transformation and regeneration in sugar beet induced by "shooter" mutants of Agrobacterium tumefaciens. Euphytica 185–194.
63. Kumagai, M. H., J. Donson, G. Delta-Cioppa, D. Harvey, K. Hanley, and L. K. Grill. 1995. Cytoplasmic inhibition of carotenoid biosynthesis with virus-derived RNA. P.N.A.S. U.S.A. 92:1679–1683.
64. Kuszala, M., V. Ziegler, S. Bouzoubaa, K. Richards, C. Putz, H. Guilley, and G. Jonard. 1986. Beet necrotic yellow vein virus: Different isolates are serologically similar but differ in RNA composition. Ann. Appl. Biol. 109:155–162.
65. Lazzeri, P. A. and P. R. Shewry. 1993. Biotechnology of cereals. In. Biotechnology and Genetic Engineering Review. 11:79–146.
66. Lemaire, O., D. Merdinoglu, P. Valentin, C. Putz, V. Ziegler-Graff, H. Guilley, G. Jonard, and K. Richards. 1988. Effect of beet necrotic yellow vein virus RNA composition on transmission by Polymyxa betae. Virology 162:232–235.
67. Liu, H.-Y., and J. E. Duffus. 1988. The occurrence of a complex of viruses associated with rhizomania of sugarbeet. Phytopathol. 78:1583 (Abst).
68. Iovic, B. R. and C. M. Rush. 1995. BNYVV-related indigenous mild viral strains for biocontrol of rhizomania: Characterization of candidate isolates and production of inoculum for field testing. Phytopathol. 85:1136.
69. Luo, Z. and R. Wu. 1988. A simple method for the transformation of rice via the pollen-tube pathway. Plant Mol. Biol. Rep. 6:165–174.
70. Maas, C. and W. Werr. 1989. Mechanism and optimized conditions for PEG mediated DNA transfection into plant pitoplasts. Plant Cell Rep. 8:148–151.
71. McCormick, S., J. Niedermeyer, J. Fry, A. Bamason, R. Horsch and R. Fraley. 1986. Leaf disc transformation of cultivated tomato (*L. esculentum*) using *Agrobacterium tumefaciens*. Plant Cell Rep. 51:81–84.
72. Ooms, G. 1992. Genetic engineering of plants and cultures. In. Plant Biotechnology, M. W. Fowler and G. S. Warren, eds. Pergamon Press, Oxford, pp. 223–257.
73. Peters, D., and A. Godfrey-Veltman. 1989. *Polymyxa betae* zoospores as vectors of beet necrotic yellow vein furovirus. Bull. OEPP/EPPO 19:509–515.
74. Prillwitz, H., and E. Schlosser. 1993. Virus-vector interactions in the Rhizomania syndrome. In: Proc. Second Symposium International Working Group on Plant Viruses with Fungal Vectors, Montreal, Canada, pp. 107–110.
75. Quillet, L., H. Guilley, G. Jonard, and K. Richards. 1989. In vitro synthesis of biologically active beet necrotic yellow vein virus RNA. Virology 172:293–301.
76. Raineri, D. M., P. Bottino, M. P. Gordon, and N. W. Nester. 1990. Agrobacterium-mediated transformation of rice (*Oryza sativa* L.) Bio/Technol. 8:33–38.
77. Richards, K., G. Jonard, H. Guilley, V. Ziegler, and C. Putz. 1985. In vitro translation of beet necrotic yellow vein virus RNA and studies of sequence homology among the RNA species using cloned cDNA probes. J. Gen. Virol. 66:345–350.
78. Richards, K. E., and T. Tamada. 1992. Mapping functions on the multipartite genome of beet necrotic yellow vein virus. Annu. Rev. Phytopathol. 30:291–313.
79. Rush, C. M., G. B. Heidel, R. C. French, and M. D. Lazar. 1993. Relationship between BNYVV and an unnamed soilborne sugar beet virus from Texas. J. Sugar Beet Res. 30:114.
80. Rush, C. M., R. C. French, and G. B. Heidel. 1993. Texas 7 a possible strain of beet necrotic yellow vein virus. In Proceedings Second Symposium International Working Group on Plant Viruses with Fungal Vectors, Montreal, Canada, pp. 59–62.
81. Rush, C. M., R. C. French, and G. B. Heidel. 1994. Differentiation of two closely related furoviruses using the polymerase chain reaction. Phytopathol. 84:1366–1369.
82. Rush, C. M. and G. B. Heidel. 1995. Furovirus diseases of sugar beets in the United States. Plan Dis. 79:868–875.
83. Rush, C. M., G. B. Heidel, and M. D. Laar. 1993. Relationship between BNYVV and an unnamed soilborne sugar beet virus from Texas. American Society of Sugar Beet Technologists Proc., Anaheim, Calif., 30:114.
84. Rush, C. M., K.-B. G. Scholthof, S. K. Manohar, and G. B. Heidel. 1996. Similarities between beet soilborne mosaic virus and beet necrotic yellow vein virus RNA2 nudeotide sequence and genomic organization. In: Proceedings Third Symposium international Working Group on Plant Viruses with Fungal Vectors, J. Sherwood and C. Rush, eds., C&M Press, Denver, Colo. (in press).
85. Rush, C. M. and J. L. Sherwood. 1996. Viral control agents. In: Environmentally Safe Approaches to Crop Disease Control, Chapter 6, J. Rechcigl, ed., CRC Press, Boca Raton, Fla. (in press).
86. Ryals, J. 1996. Agricultural biotechnology '96. Mol. Breed. 2:91–93.
87. Sambrook, J., E. F. Fritsch, and T. Maniatis. 1989. Molecular Cloning: A Laboratory Manual, 2nd ed., Cold Spring Harbor Laboratory Press, Plainview, N.Y.
88. Sanford, J. C. 1988. The biolistic process. Trends in BioTech. 6:299–302.
89. Schmitt, C., E. Balmori, G. Jonard, K. E. Richrads, and H. Guilley. 1992. In vitro mutagenesis of biologically active transcripts of beet necrotic yellow vein virus RNA 2: Evidence that a domain of the 75-kDa readthrough protein is important for efficient virus assembly. P.N.A.S. U.S.A. 89:5715–5719.
90. Scholthof, H. B., K.-B. G. Scholthof and A. O. Jackson. 1996. Plant virus gene vectors for transient expression of foreign proteins in plants. Ann. Rev. Phytopathol. 34:299–323.
91. Senaratra, T., B. D. McKersie, K. J. Kasha, and J. D. Procunier. 1991. Direct DNA uptake during the imbibition of dry cells. Plan Sci. 79:223–228.
92. Shen, W. H., and B. Hohn. 1995. Vectors based on maize streak virus can replicate to high copy numbers in maize plants. J. Gen. Virol. 76:965–969.
93. Shepherd, R. J. 1989. Biochemistry of DNA plant viruses. In. Biochemistry of Plants. A. Marcus, ed., New York Academic Press, 15:563–616.
94. Shepherd, R. J., R. J. Wakeman, R. R. Romanko, 1968, DNA in cauliflower mosaic virus. Virology 36:150–152.
95. Sherwood, J. L. 1987. Mechanisms of cross-protection between plant virus strains. In: Plant Resistance to Viruses. D. Evered and S. Harnett, eds., Wiley. Chichester, pp. 136–150.
96. Sherry, M. W., T. A. Thorpe, and M. M. Moloney. 1989. PEG-mediated expression of GUS and CAT genes in protoplasts from embryogenic suspension cultures of Picea glanca. Plant Cell Rep. 7:704–707.
97. Shirako, Y., and M. K. Brakke. 1984. Two purified RNAs of soil-borne wheat mosaic virus are needed for infection. J. Gen. Virol. 65:119–127.
98. Simon, A. E. and J. J. Bujarslid. 1994. RNA-RNA recombination and evolution in virus-infected plants. Ann. Rev. Phytopathol. 32:337–362.
99. Somers, D. A., H. W. Rines, W. Gu, H. F. Kaeppler, and W. R. Bushnell. 1992. Fertile transgenic oat plants. Bio/Technol. 10:1589–1594.
100. Stanley, J. 1993. Gemini viruses: plant viral vectors. Curr. Opin. Genet. Dev. 3:91–96.
101. Tamada, T., M. Saito, T. Kiguchi, T. Kusume. 1990. Effect of isolates of beet necrotic yellow vein virus with different RNA components on the development of rhizomania symptoms. In: Proc. First Symposium international Working Group on Plant Viruses with Fungal Vectors, Braunschweig, Germany, pp. 41–44.
102. Tamada, T., Y. Shirako, H., Abe, M. Saito, T. Kiguchi, and T. Harada. 1989. Production and pathogenicity of isolates of beet necrotic yellow vein virus with different numbers of RNA components. J. Gen. Virol. 70:3399–3409.
103. Tamada, T. 1975. Beet necrotic yellow vein virus. Commonwealth Mycol. Inst. Assoc. Appl. Biol. 144, Wm Culross and Son Ltd., Scotland.
104. Topfer, R., B. Gronenbom, J. Shell, and H. H. Steinbiss. 1989. Uptake and transient expression of chimeric genes in seed-derived embryos. Plant Cell. 2:133–139.
105. Tuitert, G. 1993. Horizontal spread of beet necrotic yellow vein virus in soil. Neth. J. Plant Pathol. 99:85–96.
106. Vander Kuyl, A. C., L. Neelman, and J. F. Bol. 1991. Complementation and recombination between alfalfa mosaic virus RNA3 mutants in tobacco plants. Virology 183:731–738.
107. Vasil, V., A. Castillo, M. Fromm, and I. Vasil. 1992. Herbicide resistant fertile transgenic wheat plants obtained by microprojectile bombardment of regenerable embryogenic callus. Bio/Technology 10:667–674.
108. Weeks, J. T., O. D. Anderson, and A. E. Blechl. 1993. Rapid production of multiple independent lines of fertile transgenic wheat (*Triticum aestivum*). Plant Physiol. 102:1077–1084.
109. Wisler, G. C., J. E. Duffus, and H.-Y. Liu. 1993. Variations among furoviruses associated with sugarbeet. In: Proc. Second Symposium of the International Working Group on Plant Viruses with Fungal Vectors, Montreal, Canada, pp. 63–66.
110. Wright, M. S., K. Launis, C. Bouman, M. Hill, J. Dimatio, C. Kramer, and R. D. Shillito. 1996. A rapid visual method to identify transformed plants. In Vitro Cell and Devel. Biol. 32:11–13.
111. Wu, G., Shortt, B. J., Lawrence, E. B., Levin, E. B., Fitzsimmons, K. C., and Shah, D. M. 1995. Disease resistance conferred by expression of a gene encoding H2O2-generating glucose oxidase in transgenic potato plants.
112. Yang, N. S. 1995. Particle bombardment technology for gene transfer into plant and mammalian systems. In Vitro Cell. and Devel. Biol. 31, 3. A:JS-6.
113. Zhang, L., A. Mitra, R. C. French, and W. G. Langenberg. 1994. Fungal zoospore-mediated delivery of a foreign gene to wheat roots. Phytopathol. 84:684–687.
114. Ziegler-Graff, V., S., Bouzoubaa, I. Jupin, H. Guilley, G. Jonard, and K. Richards. 1988. Biologically active transcripts of beet necrotic yellow vein virus RNA-3 and RNA-4. J. Gen Virol. 69:2347–2357.

What is claimed is:

1. A method for delivering a recombinant virus to a plant comprising the steps of:
   contacting seed of a first plant susceptible to infection by a soilborne fungus, with a soilborne fungus selected from the group consisting of Polymyxa and Spongospora containing a recombinant furovirus;
   growing said seed into a second plant which is susceptible to infection by said soilborne fungus;
   infecting said second plant with said soilborne fungus containing said recombinant virus, thereby delivering said recombinant virus to said second plant.

2. The method of claim 1, wherein said growing said seed into a second plant occurs about simultaneously with said infecting said second plant with said soil born fungus.

3. The method of claim 1, wherein said soilborne fungus is Polymyra.

4. The method of claim 3, wherein a furovirus is selected from the group consisting of soilborne wheat mosaic virus (SBWMV), beet necrotic yellow vein virus (BNYVV), peanut clump virus (PCV), oat golden stripe virus (OGSV), potato mop top virus (PMTV), rice stripe necrosis virus (RSNV), broad bean necrosis virus (BBNV), fern mottle virus (FMV), Hyposhoeris mosaic virus (HMV), Indian peanut clump virus (IPCV), Nictiana velutina mosaic virus (NVMV), sorghum chlorotic spot virus (SCSV), and beet soil borne mosaic virus (BSBMV).

5. The method of claim 1, wherein said soilborne fungus is selected from the group consisting of *Polymyxa betae* and *Polymyxa graminis*.

6. The method of claim 2, wherein said seed is contacted with cystosori of said soilborne fungus containing said recombinant virus.

7. The method for preparing seed for delivering a recombinant virus into a plant comprising the steps of:
 obtaining a soilborne fungus containing a recombinant virus; and
 coating seed of a first plant susceptible to infection by said soilborne fungus containing a recombinant virus, with said soilborne fungus selected from the group consisting of Polymyxa and Spongospora containing a recombinant virus, such that growing said seed into a second plant results in infecting said second plant with said soilborne fungus containing said recombinant furovirus, thereby delivering said recombinant virus to said second plant.

8. The method of claim 7, wherein said soilborne fungus is Polymyxa.

9. The method of claim 8, wherein a furovirus is selected from the group consisting of soilborne wheat mosaic virus (SBWMV), beet necrotic yellow vein virus (BNYVV), peanut clump virus (PCV), oat golden stripe virus (OGSV), potato mop top virus (PMTV), rice stripe necrosis virus (RSNV), broad bean necrosis virus (BBNV), fern mottle virus (FMV), Hyposhoeris mosaic virus (HMV), Indian peanut clump virus (IPCV), Nictiana velutina mosaic virus (NVMV), sorghum chlorotic spot virus (SCSV), and beet soil borne mosaic virus (BSBMV).

10. The method of claim 7, wherein said soilborne fungus is selected from the group consisting of *Polymyxa betae* and *Polymyxa graminis*.

11. The method of claim 7, wherein said seed is coated with cystosori of said soilborne fungus containing said recombinant virus.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 14 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:1:

TTCACAAGTC AGTA                                              14

(2) INFORMATION FOR SEQ ID NO:2:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:2:

AGATAGTGCT ATAAACGG                                          18

(2) INFORMATION FOR SEQ ID NO:3:

(i) SEQUENCE CHARACTERISTICS:
    (A) LENGTH: 21 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:3:

TACGCAACTC ATTGAAAGGT A                                      21

(2) INFORMATION FOR SEQ ID NO:4:

(i) SEQUENCE CHARACTERISTICS:
    (A) LENGTH: 21 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:4:

AGATAACACT TGTAACTCGT C                                      21